United States Patent [19]
Vancaillie et al.

[11] Patent Number: 5,944,668
[45] Date of Patent: Aug. 31, 1999

[54] SURGICAL FLUID AND TISSUE LOSS MONITOR

[75] Inventors: Thierry G. Vancaillie, San Antonio, Tex.; Robert K. Mitchiner, Longmont; David W. Newton, Boulder, both of Colo.

[73] Assignee: Aquintel Corporation, Mountain View, Calif.

[21] Appl. No.: 09/008,099

[22] Filed: Jan. 15, 1998

Related U.S. Application Data

[60] Division of application No. 08/645,349, May 13, 1996, which is a continuation-in-part of application No. PCT/US95/14101, Oct. 31, 1995, Pat. No. 5,709,670, which is a continuation-in-part of application No. 08/484,877, Jun. 7, 1995, Pat. No. 5,522,805, which is a continuation-in-part of application No. 08/237,350, May 3, 1994, Pat. No. 5,492,537.

[51] Int. Cl.$^6$ .................................................... A61B 5/00
[52] U.S. Cl. ........................ 600/477; 600/322; 604/246
[58] Field of Search ................................ 604/4, 20, 246, 604/318; 600/309, 310, 315, 316, 318, 322, 326, 328, 573, 476, 477

[56] References Cited

U.S. PATENT DOCUMENTS

| | | |
|---|---|---|
| 4,994,026 | 2/1991 | Fecondini . |
| 5,112,298 | 5/1992 | Prince et al. . |
| 5,135,485 | 8/1992 | Cohen et al. . |
| 5,152,746 | 10/1992 | Atkinson et al. . |
| 5,178,606 | 1/1993 | Ognier et al. . |
| 5,200,345 | 4/1993 | Young . |
| 5,200,627 | 4/1993 | Chevallet . |
| 5,211,849 | 5/1993 | Kitaevich et al. . |
| 5,226,313 | 7/1993 | Murata et al. . |
| 5,234,608 | 8/1993 | Duff . |
| 5,236,664 | 8/1993 | Ludvigsen . |
| 5,285,682 | 2/1994 | Micklish . |
| 5,312,334 | 5/1994 | Hara et al. . |
| 5,328,478 | 7/1994 | McVay . |
| 5,331,958 | 7/1994 | Oppenheimer . |
| 5,333,610 | 8/1994 | Hirao ...................................... 600/310 |
| 5,344,568 | 9/1994 | Kitaevich et al. . |
| 5,372,709 | 12/1994 | Hood . |
| 5,376,070 | 12/1994 | Purvis et al. . |
| 5,395,321 | 3/1995 | Kawahara et al. . |
| 5,421,812 | 6/1995 | Langley et al. . |
| 5,437,629 | 8/1995 | Goldrath . |
| 5,445,610 | 8/1995 | Evert . |
| 5,458,567 | 10/1995 | Cathcart . |
| 5,471,981 | 12/1995 | Wiggins et al. ......................... 600/309 |
| 5,492,537 | 2/1996 | Vancaille . |
| 5,503,626 | 4/1996 | Goldrath . |
| 5,522,805 | 6/1996 | Vancaillie et al. ....................... 604/246 |
| 5,553,613 | 9/1996 | Parker ................................. 600/322 X |
| 5,582,169 | 12/1996 | Oda et al. ........................... 600/322 X |
| 5,586,973 | 12/1996 | Lemaire et al. .......................... 604/19 |
| 5,676,142 | 10/1997 | Miwa et al. ........................ 600/309 X |

FOREIGN PATENT DOCUMENTS

WO 92/18049  10/1992  WIPO .

OTHER PUBLICATIONS

Ankum, W.M., and Vonk, J., 1994. "The spring balance: a simple monitoring system for fluid overload during hysteroscopic surgery," *The Lancet* 343:836–7.

McDonald, H.P. "An Automatic Peritoneal Dialysis Machine for Hospital or Home Peritoneal Dialysis: Preliminary Report", Trans. Amer. Soc. Artif. Int. Organs, 15:108–113, 1969.

Shirk, G.J. and Gimpelson, R.J., 1994. "Control of intrauterine fluid pressure during operative hysteroscopy," *J. Am. Assoc. Gynecol. Lapro.* 1(3):229–33.

*Primary Examiner*—Ronald Stright
*Assistant Examiner*—A. T Nguyen
*Attorney, Agent, or Firm*—Fish & Richardson P.C.

[57] ABSTRACT

A monitor to provide substantially real-time estimates of fluid absorption rate and tissue loss rate in a patient during a surgical procedure. The monitor estimates fluid source flow rates and waste fluid flow rates based on weight changes per unit time or direct reading fluid flow rate meters. Tissue loss flow rates are estimated based on tissue concentration measurable in waste irrigation fluid using an optical comparator, and are used to correct waste fluid flow rates. Correct waste fluid flow rates are used in turn to obtain estimated fluid absorption rates.

1 Claim, 14 Drawing Sheets

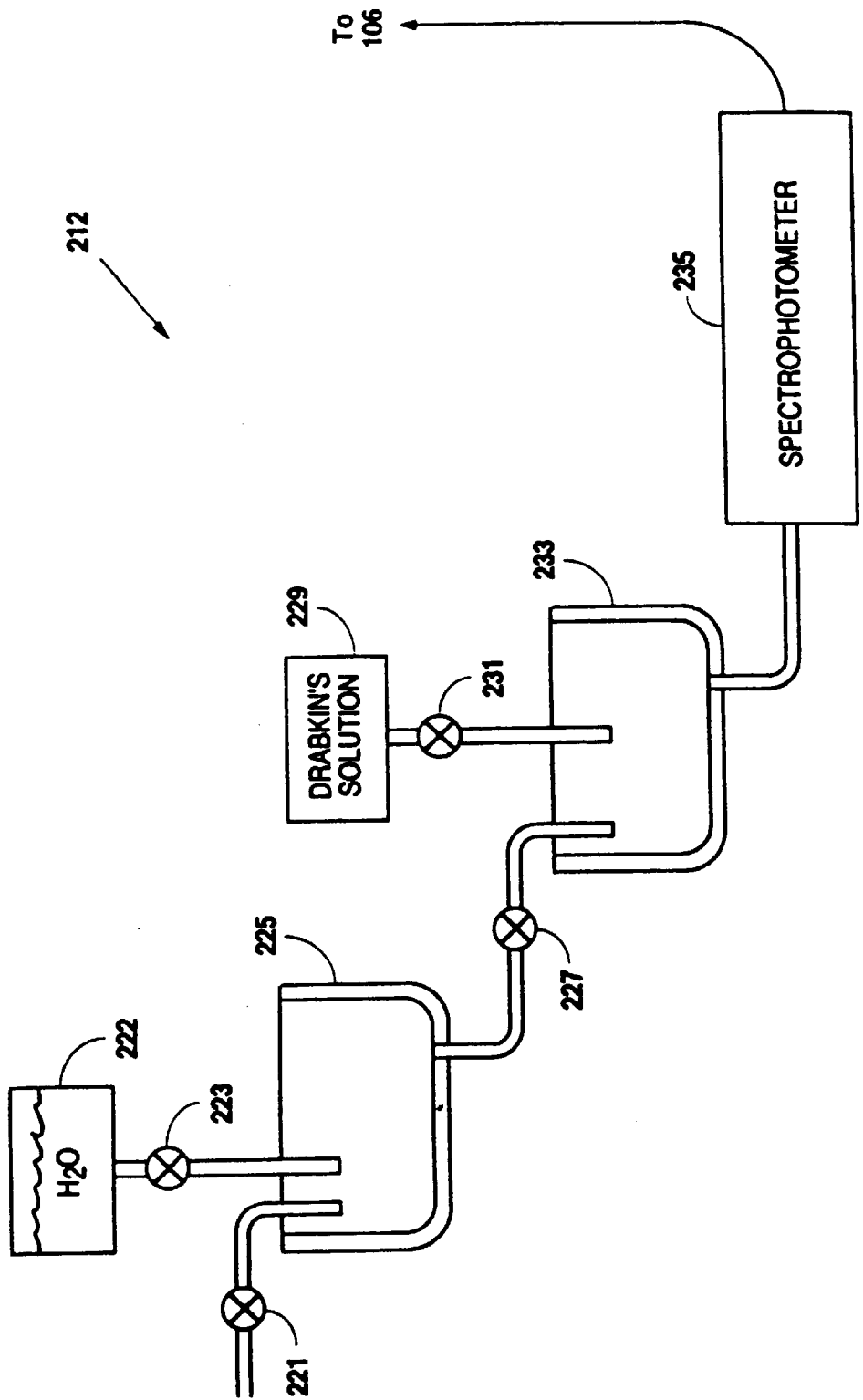

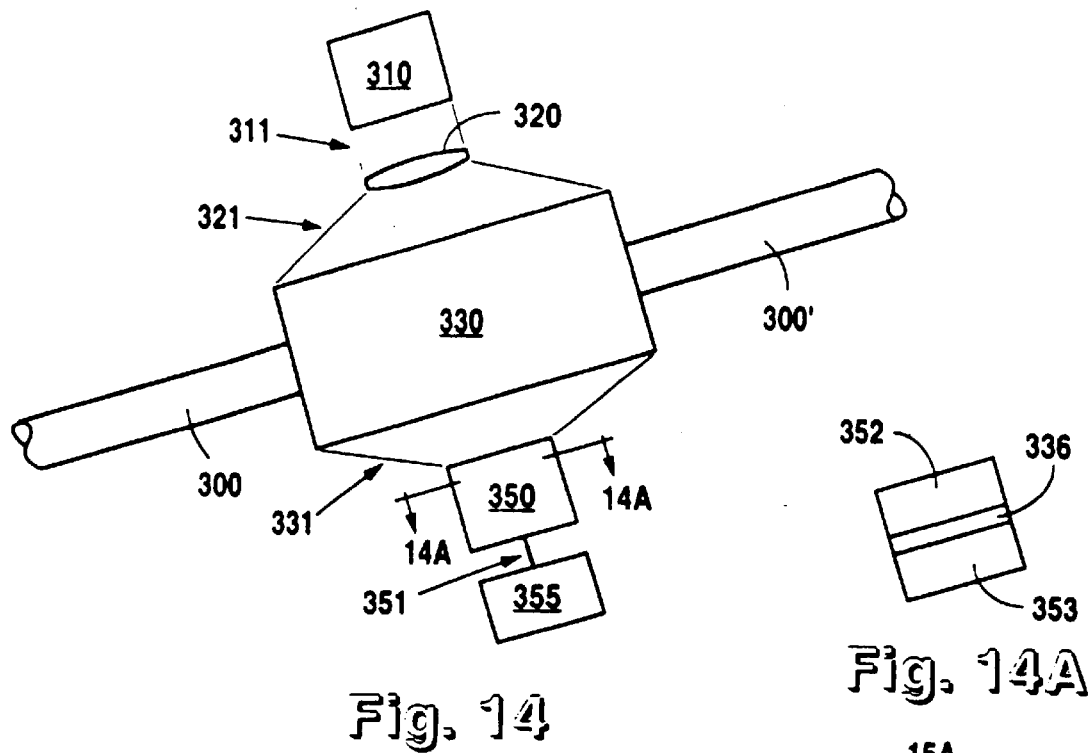
Fig. 14
Fig. 14A
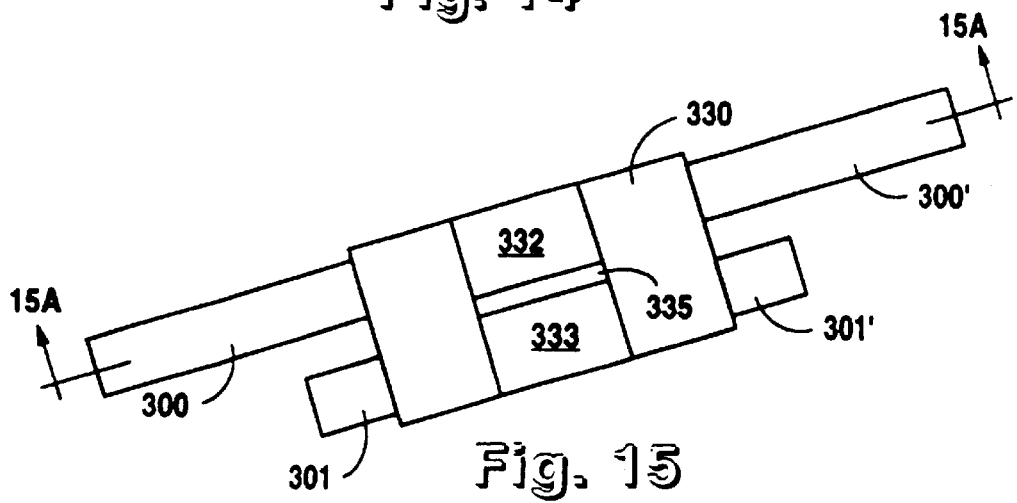
Fig. 15
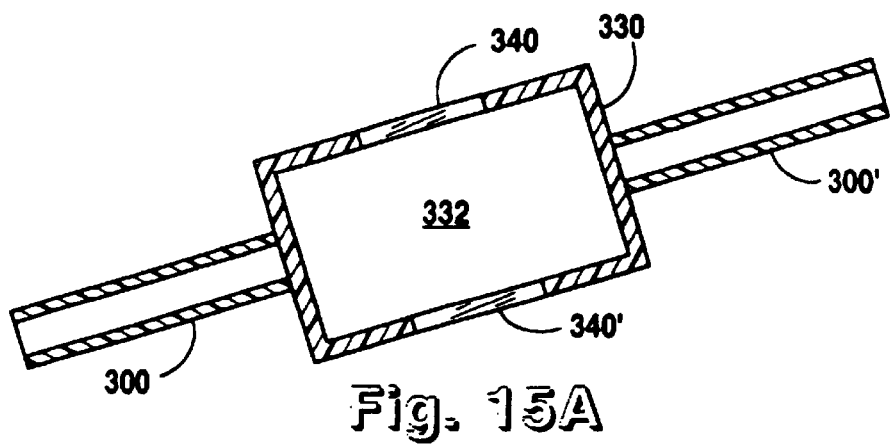
Fig. 15A

SURGICAL FLUID AND TISSUE LOSS MONITOR

This is a divisional of U.S. application Ser. No. 08/645,349, filed May 13, 1996, now U.S. Pat. No. 5,709,670.

Which is a continuation-in-part of PCT application Ser. No. PCT/US95/14101 filed Oct. 31, 1995, which is a continuation-in-part of application Ser. No. 08/484,877 filed Jun. 7, 1995, now U.S. Pat. No. 5,522,805 which is a continuation-in-part of application Ser. No. 08/237,350 filed May 3, 1994, now U.S. Pat. No. 5,492,537.

BACKGROUND

FIELD OF THE INVENTION

The invention relates to methods and apparatus for estimating rates and volumes of irrigation fluid absorption and/or tissue loss by a patient during a surgical procedure.

Physiological Fluid Compartments

Total body water, which represents about 45% of total body weight in women and about 50% of total body weight in men, may be regarded as occupying primarily three physiological volumes or compartments. The largest of these three compartments, intracelular water, accounts for about 30–35% of total body weight. The two smaller compartments, which together comprise extracellular volume, are interstitial volume (about 10–12% of total body weight) and plasma volume (about 4–5% of total body weight). Plasma volume, in turn, is about 60–70% of blood volume with the remainder of blood volume being substantially occupied by formed elements such as red and white blood cells.

During surgery, optimal patient care requires maintaining the plasma/blood ratio, plasma osmolality, and plasma electrolyte levels within fairly narrow ranges. Note that if a portion of the plasma is replaced by an equal volume of water, the plasma/blood ratio may stay constant while plasma osmolality and electrolyte concentrations will decrease. On the other hand, adding water to a fixed volume of blood will both dilute the plasma (thus lowering its osmolality and electrolyte levels) and increase the plasma/blood ratio. Keeping plasma osmolality in a normal range helps assure that cells neither lose nor gain too much water by osmosis, while maintaining plasma electrolyte levels is important for normal cellular function (especially in neurons). The plasma/blood ratio strongly affects both blood flow characteristics and oxygen delivery to the tissues. Thus, significant blood loss and/or fluid absorption in surgical patients is preferably monitored in real time to detect unfavorable changes and allow timely corrective action.

Blood Loss and Fluid Absorption During Surgery

Blood lost during open surgery usually is blotted with surgical sponges or washed away from the surgical site with a stream of sterile irrigation fluid. Clinically significant blood loss may be monitored by weighing sponges and visually estimating the amount of blood flowing into the wound. During endoscopic surgery, on the other hand, virtually all lost blood is carried away in the irrigation fluid where it is difficult to quantify.

Nevertheless, endoscopic and other substantially closed procedures (including liposuction) which carry a risk of significant blood loss are becoming more common. Previously well-known endoscopic procedures (such as hysteroscopy, cystoscopy, gastroscopy, colonoscopy and bronchoscopy) are now augmented by new endoscopic applications because of the promise of shorter recovery times and reduced patient morbidity. Increasing numbers of traditionally open surgical procedures (for example, in intra-abdominal, intra-articular and intra-thoracic operations) are also being done endoscopically.

Aiding this transition are recent dramatic improvements in surgical instruments. An endoscope inserted through a natural orifice or a small incision into a body cavity or potential space gives the surgeon a remarkably clear real-time view of the operative site. The endoscope may incorporate ports for the introduction of other surgical instruments and irrigation fluid, and/or for the removal of waste irrigation fluid, blood and small tissue fragments from the surgical site. One or more additional or alternative ports communicating with the operative site may also be used. The latter ports may comprise natural and/or artificial tracts, passages or orifices, and are typically used in conjunction with an endoscope to facilitate fluid flow to or from the operative site and/or to admit surgical instruments or allow removal of relatively large pieces of excised tissue.

Because of the superior control of fluid flows inherently available in substantially closed surgical cases (including endoscopic procedures), surgeons can theoretically monitor substantially all fluid exchange experienced by a patient during an operation. The potential advantages of such monitoring in reducing the incidence and severity of complications have also led to heightened interest in reexamining fluid monitoring for surgical patients undergoing open procedures. Unfortunately, equipment that would allow such generalized fluid monitoring to be widely practiced has not been commercially available until recently. Among other reasons for its absence are the volumetrically offsetting effects of blood loss and irrigation fluid absorption in a patient, making these latter measurements difficult to determine in light of uncertainty in measured volumes of irrigation fluid dispensed and recovered.

To understand the difficulty, we note that fluid flow control is commonly used to direct and/or maintain a flow of irrigation fluid across the operative site to ensure the surgeon's clear view by splinting the operative space open and/or by continuously carrying away blood (a type of tissue) and small fragments of other types of tissue. By maintaining at least an intermittent flow of relatively low-pressure (frequently electrically non-conducting) irrigation fluid from an external reservoir into the operative site (such as a body cavity), and simultaneously (usually at substantially the same flow rate) withdrawing irrigation fluid from the operative site, optimal operating conditions can be maintained. However, important physiological changes associated with fluid shift may be taking place during the operation; they can seriously affect both inteperative patient safety and the course of postoperative recovery.

For example, while the irrigation fluid flow serves admirably to keep the operative site clear, it tends to mask the true amount of blood loss because lost blood is continuously diluted and carried away. Simultaneously, irrigation fluid and/or components thereof may be absorbed through intact membranes or into portions of the vascular systems (blood and/or lymph) which have been opened by the surgery. The largest component of irrigation fluid (that is, water) is often of greatest concern for reasons described above. But other components, such as local anesthetics which are commonly added to irrigation fluid during liposuction, can be toxic in relatively small quantities when they are preferentially adsorbed or absorbed by tissue surfaces. The total amount of such drugs remaining in the body as well as the time period over which they are accumulated are both important to making informed patientcare decisions related to the surgery.

For example, to optimally maintain a patient's hemodynamic stability during and after an operation, clinically significant volumes of blood lost should be replaced, usually by intravenous administration of crystalloid and/or colloid solutions (possibly including blood and/or blood products) in empirically determined proportions relative to the amount of blood lost. At the same time blood is being lost, however, irrigation fluid is being absorbed. Absorbed irrigation fluid components can expand intravascular volume, reduce the colloid osmotic pressure of the blood, dilute blood coagulation factors, alter the patients' preoperative blood electrolyte concentrations, and in some cases impose a toxic burden (as from excessive local anesthetic). The latter conditions may predispose the patient to further blood loss, pulmonary edema, seizures, coma and death.

Thus, the amount and type of intravenous replacement fluids given (including components such as anesthetics) which can materially alter intravascular volume, fluid distribution, and neurological status, should be governed in part by accurate, real-time assessment of actual blood and other tissue loss, with compensation as necessary for absorption and redistribution of irrigation fluid. In this regard, it should be noted that absorption of irrigation fluid as, for example, through the peritoneum, occurs at a relatively slow and predictable rate, while that through highly vascular tissue undergoing surgery, such as the uterine lining, may be much more rapid. Similarly, significant blood loss may occur over a relatively short period of time (as from a severed artery), or may develop as a prolonged ooze (as from necrotic tissue to be excised). Thus, algorithms for determining the above compensation can be expected to vary with time in any given patient and also to vary with the type of surgery.

For certain patients, such as those in heart or renal failure who may be particularly sensitive to edema and/or changes in intravascular volume, real-time knowledge of the rate of blood loss can reduce the likelihood of intraoperative and/or postoperative complications by allowing adjustment of intravenous fluid administration types and rates to maintain hemodynamic stability. Accurate blood loss estimates can also guide fluid replacement therapy to maintain adequate hemostasis and to improve rheological conditions and oxygenaying capacity for maximizing the flow of well-oxygenated blood to the tissues. It should be noted here that the patient's intraoperative clearance of free water through the kidneys, as well as redistribution of free water within the extracellular space (third spacing fluid in, for example, edema, ascites, and/or pleural effusion) will affect the preferred crystalloid/colloid ratio for intravenously administered fluids. This ratio can be expected to vary over the course of relatively long operations.

Failure to maintain adequate hemostasis can result in catastrophic blood loss, and failure to maintain sufficient oxygenation and/or intravascular volume can result, for example, in shock, possibly leading to tissue necrosis and/or cardiac arrest Excessive intravascular volume, on the other hand, may lead to pulmonary edema and respiratory arrest Whether or not a given patient will actually hemorrhage, arrest or develop any other complication depends on factors such as the patient's initial cardiovascular status, the amount and rate of onset of fluid shifts in the cardiovascular system, and the initial fluid volume status of the patient. Thus, careful monitoring of blood loss and fluid absorption for each patient in real time may help reduce morbidity and mortality when combined with other preoperative and interoperative assessments.

Estimation of Fluid Flow Rates

Conventional measurement of total fluid volume infused through an intravenous catheter is relatively easy, although subject to about 10% reading error when collapsible plastic fluid containers are used. In contrast, estimation of the volume of blood loss is error-prone because a mixture of blood and irrigation fluid may drain substantially continuously from the operative site. Draining fluid is commonly distributed over the surgical drapes, operating table, and floor, as well as to containers resting on the floor. Incidental absorption by and adsorption to various operating-room surfaces, as well as losses in handling due to spillage and splashing, have made irrigation fluid recovery uncertain in the past. Accurate estimation of the blood loss rate and the total blood volume contained in irrigation fluid recovered under these conditions is, of course, problematical, and the clinical usefulness of such estimates is very limited.

A more convenient and more accurate method of estimating blood loss using equipment previously described requires careful collection of waste irrigation fluid. By hanging irrigation fluid source bags and a waste irrigation fluid collector bucket on the same spring scale and then directly and automatically comparing a decrease in source fluid weight with an increase in collected fluid weight, one may estimate net fluid weight gain or loss. Over relatively short periods of time, assuming absorption of irrigation fluid is negligible compared to blood loss, irrigation fluid removed from the source should substantially equal irrigation fluid recovered from the collector. Thus, any indicated weight gain in the source-collector system would be largely due to the volume of blood loss, which is added to the volume of irrigation fluid collected.

This suspended system, while simple, is undesirable because errors in estimated blood loss due to fluid absorption are virtually undetectable. The system is also inconvenient because it is fixed to an overhead support (as, for example, in the ceiling). Additionally, such a suspended system has a tendency to rotate around the suspension member, kinking source and/or drainage tubes and complicating weight measurements because of varying lateral and vertical load components. Accurate weights can only be obtained if the suspended system is actually vertical, but in general it will not be because of the lateral forces applied by the various fluid lines attached to it. Finally, since previously described suspended systems do not provide for independent determination of irrigation source fluid and waste irrigation fluid flow rates and blood loss rate, fluid therapy must be empirical. Without reasonably accurate estimates of absorbed fluid and blood loss flow rates, the optimal balance of crystalloid, colloid and blood products in the fluid therapy for each surgical patient becomes a clinical judgment subject to considerable error. Further, the presence of tissue other than blood (such as fat) in waste irrigation fluid can compound errors in estimates of blood loss and fluid absorption.

SUMMARY OF THE INVENTION

The present invention answers the need for apparatus and methods to provide accurate and substantially real-time estimates of absorbed irrigation fluid flow rate and volume, as well as blood loss rate and volume and other tissue losses experienced by a patient during a surgical procedure (either open or substantially closed). When blood loss is not clinically significant, estimates of irrigation fluid volume absorption per unit time (that is, fluid absorption rate) by a patient are obtained by subtracting an estimate of waste irrigation fluid volume collected per unit time (that is, waste irrigation fluid flow rate) from an estimate of irrigation fluid volume flow from one or more sources per unit time (that is, irrigation fluid source flow rate). These flow rate estimates are preferably based on a series of weight measurements over time sequentially differenced to yield weight change per unit time (which, divided by the fluid density, then yields volume change per unit time). Alternatively, flow rate estimates may be based on direct measurement of volume change per unit time (as by serial readings over time of a fluid level indicator in a fluid storage tank) and/or on at least one direct-reading fluid flow rate meter in the relevant fluid stream. Commercially available direct-reading flow rate meters may incorporate, for example, a venturi or turbine-tachometer to indicate flow velocity in a fluid passage of known cross-sectional area. Where a fluid flow includes formed elements (as in the flow of waste irrigation fluid containing blood or small tissue fragments), doppler flow meters may be used to estimate fluid flow velocity as being substantially equal to the indicated velocity of the formed elements which are observed using the doppler meter. Flow velocity, in turn, may be multiplied by a conversion function characteristic of the known fluid passage area to yield flow rate (that is, flow volume per unit time). For conversion of fluid weight changes per unit time to fluid volumes per unit time, it is convenient in applications which do not clinically require greater accuracy to approximate the density of physiological fluids and irrigation fluids as that of water or 1 g/ml. Using this approximation, fluid weight changes measured in g/min will be substantially numerically equal to the corresponding volume changes measured in ml/min.

When waste irrigation fluid contains blood, a blood loss flow rate is preferably independently estimated, and the waste fluid flow rate is then corrected by subtraction of the estimated blood loss flow rate to yield a corrected waste fluid flow rate. Similarly, when waste irrigation fluid contains fat or other tissue in a relatively finely divided form (such as micelles, particles, and/or small formed elements) loss rates for each respective tissue type are preferably independently estimated, with the waste fluid flow rate then being corrected as needed by subtraction of each relevant estimated tissue volume flow rate to yield a corrected waste fluid flow rate. Total volume flows (fluid and/or particulate) for any desired time period are obtained by integrating (as a substantially smooth or piecewise continuous function) the relevant volume flow rate with respect to time over the period in question. Total volume flows for a time interval comprising two or more successive time periods can analogously be obtained by summing the total volume flows (that is, the integrated flow rate) for each of the successive time periods comprising the time interval. Integration means for accomplishing the above integration may be included within computing means and preferably include, but are not limited to, standard algorithms for digital integration stored in a digital computer memory (and thereby coupled to the digital computer), electronic analog integrators comprising one or more operational amplifiers coupled to a digital computer by appropriate analog-to-digital converters and digital-to-analog converters, and mechanical integrators having digital position and velocity sensors coupled to a digital computer. Integration means may optionally additionally comprise mechanical and/or electrical low-pass filters and/or digital noise rejection algorithms appropriately coupled to a digital computer as above and substantially simulating low-pass filters for rejecting artifacts in weight, volume and/or flow rate data. Filter characteristics exhibited by the integration means, including the upper cut-off frequency and roll-off rate are substantially empirically determined by the flow mechanics (including resonant frequencies) of the fluid supply and collection systems, as well as the desired sensitivity of the artifact rejection function.

Independent blood loss flow rate estimates may be obtained through use of hemoglobin concentration estimation means which periodically or continuously measure the hemoglobin concentration in the waste irrigation fluid. Multiplication of hemoglobin concentration by the estimated waste fluid flow rate yields a lost hemoglobin flow rate. Division of this lost hemoglobin flow rate by the patient's actual hemoglobin concentration yields an estimated blood loss flow rate. For example, if the waste irrigation fluid flow rate is 4 dl/min and the hemoglobin concentration in the waste irrigation fluid is 1.5 g/dl, then the hemoglobin flow rate is about 6 g/min (that is, (4 dl/min)×(1.5 g/dl)). If the patient's hemoglobin concentration is 12 g/dl, then the blood loss flow rate for this patient would be estimated at about 0.5 dl/min (that is, (6 g/min)÷(12 g/dl)). As a check, the estimated blood loss flow rate (0.5 dl/min) would, when multiplied by the starting hemoglobin concentration (12 g/dl), yield the calculated hemoglobin loss flow rate (6 g/min).

Hemoglobin concentration estimation means provide the hemoglobin concentration measurements needed for the above procedure, the means comprising a hemoglobin analyzer using techniques as described herein and other analogous methods well known to those skilled in the art. For example, erythrocytes in the waste irrigation fluid may be subjected to osmotic or complement-induced cytolysis, followed by chemical conversion of the free hemoglobin to another colored compound (such as acid hematin or cyanmethemoglobin) which is not sensitive to the oxygen tension in the surrounding fluid. Following this chemical conversion, the concentration of the new compound (and thus that of the original hemoglobin) can be determined by colorimetry, and the estimated blood loss flow rate calculated as described above.

An alternative hemoglobin concentration estimation means (which, with modifications described herein, is also useful for estimating fat concentration) comprises apparatus for estimating hemoglobin concentration in a sample of waste irrigation fluid following cytolysis of red blood cells in the sample as follows. Absorption by the sample of light from a source preferably capable of producing monochromatic light or light at two or more discrete source wavelengths (preferably including a wavelength of about 805 nm) is measured (as in a spectrophotometer or analogous instrument such as the optical comparator of the present invention) and compared (using comparing means) with light absorption (at substantially the same wavelength) in a fluid reference standard (such as irrigation fluid containing no hemoglobin or fat or having a known hemoglobin concentration greater than zero). Comparing means comprises means to estimate hemoglobin concentration and/or fat concentration in the waste fluid sample. Hemoglobin concentration is estimated by simply looking up in a table (manually or automatically, with or without interpolation) the hemoglobin concentration in a reference standard having substantially the same light absorption characteristic as the sample. Note that the absorption characteristic relates to a change or the absence of change in a parameter of the light (such as its intensity or wavelength) emanating from the fluid sample and/or the fluid reference standard as a result of interception by the sample and/or standard of light originating from the above source. Regarding the latter parameter, reradiation of intercepted light at substantially the same or different frequencies may be particularly useful in detecting and/or quantifying certain components of irrigation fluid. Use of a light source having a wavelength of about 805 nm in this procedure substantially obviates differences in absorption due to varying states of blood oxygenation, and the estimated hemoglobin concentration can be used as above to estimate blood loss flow rate.

Concentration estimation means for fat analogous to that above (for hemoglobin) comprises analogous apparatus and allows estimation of fat loss rate and integrated fat loss using analogous procedures. Light absorption by the fluid sample (preferably at one or more wavelengths complementary to the yellowish white of fat) is measured (as in a spectrophotometer or analogous instrument such as the optical comparator of the present invention) and compared (using comparing means) with light absorption (at substantially the same wavelength(s)) in a fluid reference standard (such as irrigation fluid containing no fat or hemoglobin). This comparison is a method to estimate fat concentration in the waste fluid sample by simply looking up in a table (manually or automatically, with or without interpolation) the fat concentration in a reference standard having substantially the same light absorption characteristic as the sample. Fat concentration in waste irrigation fluid, when multiplied by waste irrigation flow rate yields fat loss rate. Fat loss rate, in turn, may be integrated to yield fat loss. Note that in any use of a spectrophotometer, a calorimeter or the optical comparator of the present invention to assess differences in the interaction of light with a waste irrigation fluid sample and a reference standard, air bubbles will preferably be removed from all fluid samples prior to their introduction to the comparator. Additionally, since red cell cytolysis may be incomplete and since particulate tissue debris will often be present in waste irrigation fluid samples, the comparator of the present invention will preferably comprise adjustable diffuser means which are often but not necessrily located between a light source and at least two comparator fluid chambers. The adjustable diffuser means allows variable scattering of at least a portion of the light from the source to produce variably scattered light emanating from the diffuser means. At least a portion of the variably scattered light emanating from the adjustable diffuser means is subsequently intercepted by the comparator sample and reference standard fluid chambers to produce output light emanating from each of the chambers. Output light emanating from the chambers (as a result of light originally emanating from the source) finally impinges on a detector comprising a plurality of light receptors (at least one light receptor corresponding to each fluid chamber) within a detector. Light receptors are preferably photovoltaic or analogous devices which produce a signal proportional to a parameter of the light striking the receptor (such as its intensity or frequency or some function of intensity and/or frequency). Adjustment of the diffuser means variably scatters intercepted light, changes the angle and/or focus of light rays entering a comparator fluid chamber from the light source, thus changing the comparator's sensitivity to particulate matter (such as blood clots and/or cellular debris) within a fluid chamber. Difffuser means adjustment may be manually or automatically controlled through focus adjustments in a lens system and/or the insertion of light scattering sites in a light path comprising substantially transmissive optical elements and/or substantially reflective optical components. The latter function may be accomplished, for example, by use of liquid crystal or analogous electro-optical devices in transmission and/or reflectance modes.

An alternative method of estimating blood loss flow rate which does not require red blood cell cytolysis involves counting cells and estimating their volume as a fluid sample passes through an orifice (as in certain commercially available cell counter). Forming a ratio of the waste irrigation fluid cell count per unit volume to the analogous count performed on the patient's whole blood and multiplying this ratio by the patient's original (preoperative) hemoglobin concentration yields an estimate of the waste irrigation fluid hemoglobin concentration. The latter value may be used as described above to yield hemoglobin flow rate and the corresponding blood loss flow rate.

As noted above, one may estimate cell volume while obtaining the cell count per sample volume with an orifice-type cell counter. Calculating a mean cell volume, multiplying it by the cell count per sample volume, and dividing the product by the sample volume itself yields a calculated estimate of the waste fluid sample hematocrit. This sample hematocrit can then be used as a means to estimate hemoglobin concentration in the waste fluid (see below), or it can be used to estimate blood loss flow rate by reference to the patient's preoperative hematocrit. In the latter case, a hematocrit ratio of the calculated fluid sample hematocrit to the patient's preoperative hematocrit may be formed. Multiplying the hematocrit ratio by the waste fluid flow rate yields an estimate of blood loss flow rate.

Note that the calculated fluid sample hematocrit may be divided by approximately 3 to estimate the fluid sample hemoglobin concentration, a more exact divisor value being obtainable from preoperative measurements on a patient's own blood. Again, the estimated fluid sample hemoglobin concentration can be used as above to estimate blood loss flow rate.

As noted, the total blood lost (or fluid absorbed) in any given time period can be estimated by integrating the calculated blood loss flow rate (or fluid absorption rate) with respect to time over the time period in question. Total blood loss (or fluid absorption) for an operation, or for any number of successive time periods during the operation, can be obtained by summing the total blood lost (or fluid absorbed) in each of such successive periods to be considered. Preferred periods of time may be defined, for example, by the time between changes of irrigation fluid supply containers and/or waste irrigation fluid collectors. Summing fluid flows, whether of lost blood or irrigation fluid absorbed during surgery, is a function which is preferably done automatically by computing means comprising a programmable digital computer and additionally comprising, in certain embodiments, integration means coupled to the digital computer.

Note that integration means may comprise digital and/or analog components. For example, cell counts may preferably be summed and/or integrated with respect to time using digital methods well known to those in the art. On the other hand, calorimeters, spectrophotometers and comparators of the present invention may produce analog output signals which can be directly compared and/or integrated in an analog form without prior conversion to digital form using techniques well known to those in the art. Such direct signal processing may be advantageous in simplifying signal routing in the current invention and in reducing the cost of certain embodiments of the invention.

BRIEF DESCRIPTION OF THE DRAWINGS

FIG. 13 schematically illustrates the functional design of a hemoglobin analyzer.

FIG. 14 schematically illustrates the functional design of an optical comparator.

FIG. 14A schematically illustrates the cross-sectional view A—A of the comparator detector of FIG. 14.

FIG. 15 schematically illustrates a side elevation of two comparator fluid chambers.

FIG. 15A schematically illustrates the cross-sectional view A—A of the comparator fluid chambers of FIG. 15.

DETAILED DESCRIPTION

Figure 1:
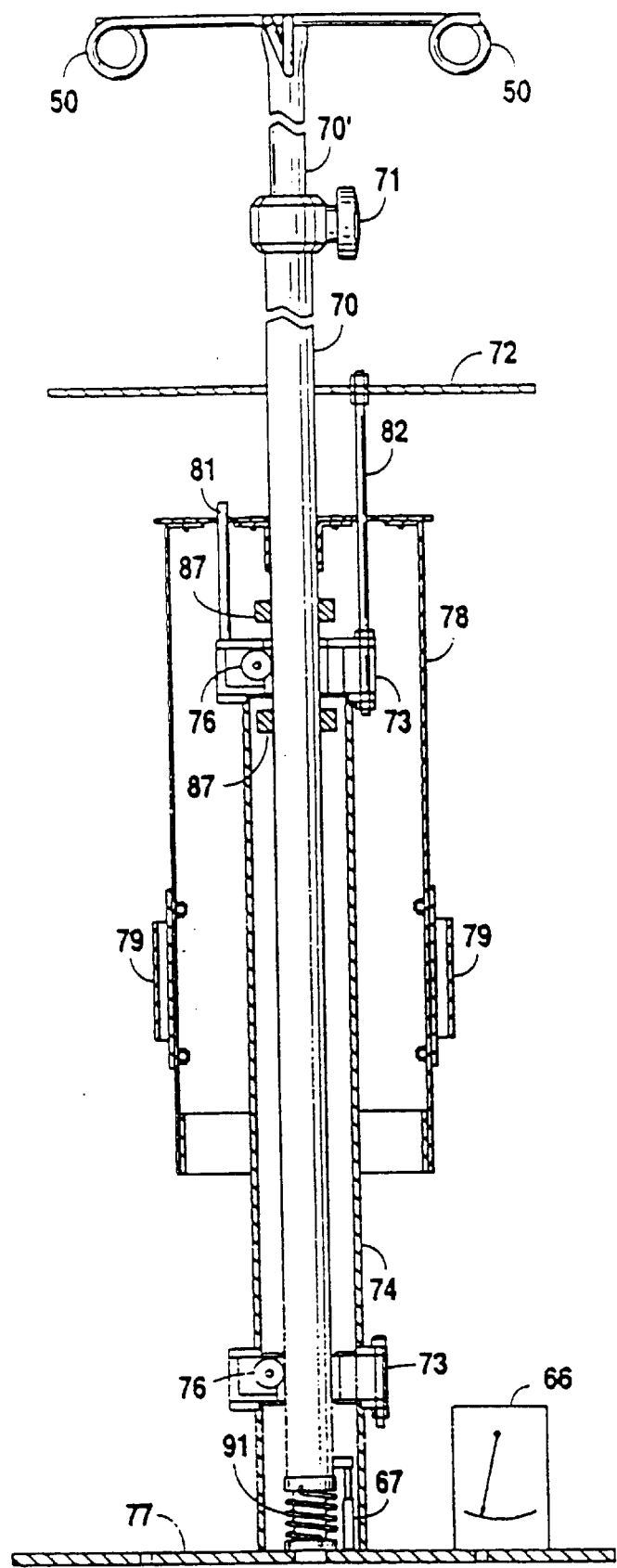
FIG. 1 schematically illustrates a preferred arrangement for source fluid supports and fluid collector supports on a fluid support column bearing on a single weight sensitive element.

In the present invention, weight-based (based on weight change per unit time) or volume-based (based on volume change per unit time) or direct-reading fluid flow rate measurements, made electronically on command or automatically (as by computing means as described herein), obviate errors inherent in any manual recording or reading of scales. Note that certain embodiments of the invention provide for a series of weight-based measurements over time of a liquid quantity which computing means (using, for example, a processor's internal clock) can sequentially difference to yield weight change per unit time of the liquid quantity in question. These weight-based measurements must be converted to volume measurements (that is, divided by the density of the liquid in question) which, when sequentially differenced, will form (again using a processor's internal clock) a flow rate for the liquid in question (that is, liquid volume change per unit time); this calculation of flow rate measurements from a series of corresponding time and weight measurements is also preferably done automatically as above. The result is greater clinical reliability when compared to conventional methods of blood loss monitoring. If virtually all blood lost from the patient appears in the waste irrigation fluid, and virtually all waste irrigation fluid is collected (preferably directly from the endoscope drain or other waste irrigation fluid drain), the absorbed fluid flow rate under steady-state conditions would be obtained by subtracting from the irrigation fluid source flow rate the corrected waste irrigation fluid flow rate, the corrected rate being defined as consisting of the waste irrigation fluid flow rate minus the blood loss flow rate. This is equivalent to summing the blood loss flow rate and the irrigation fluid source flow rate and then subtracting the waste irrigation fluid flow rate from the sum.

A preferred embodiment of the surgical fluid monitor for use where clinically significant blood flow is not expected thus comprises at least one weight-sensitive fluid source support for simultaneously suspending and weighing a fluid source and producing a signal indicative of fluid source weight. There is also at least one weight-sensitive waste fluid collector support for simultaneously suspending and weighing a waste fluid collector and producing a signal indicative of waste fluid collector weight. Computing means are coupled through input/output interfaces to the fluid source weight signal and to the waste fluid collector weight signal for calculating an estimated fluid source flow rate, an estimated waste fluid flow rate, and an estimated fluid absorption rate equal to the estimated fluid source flow rate minus the estimated waste fluid flow rate, and for producing a display signal indicative of the estimated fluid absorption rate. Fluid flow rates for all embodiments of the invention are preferably calculated by one or more of the methods described herein. Display means are coupled to the computing means for transducing for human observation the fluid absorption rate display signal.

Embodiments of the surgical fluid monitor described above and the surgical fluid and blood loss monitor described below may additionally comprise verticality compensation means to correct estimated fluid source flow rate and estimated waste fluid flow rate. Further each weight-sensitive fluid source support and each weight-sensitive waste fluid collector support preferably comprise at least one solid-state load cell, and the monitor may additionally comprise at least one anti-rotation device. When absorbed fluid volume measurements are desired, the above surgical fluid monitor and/or the surgical fluid and blood loss monitor described below additionally comprise integration means within the computing means for estimating absorbed fluid volume. The computing means then additionally produces a display signal indicative of the absorbed fluid volume, and the display means additionally transduces for human observation the absorbed fluid volume display signal. When blood loss volume measurements are desired, the surgical fluid and blood loss monitor described below additionally comprises integration means within the computing means for estimating blood loss volume, the computing means additionally producing a display signal indicative of the blood loss volume, and the display means additionally transducing for human observation the blood loss volume display signal.

The above surgical fluid monitor may be converted to a surgical fluid and blood loss monitor which comprises, in addition to the weight-sensitive fluid source support(s) and weight-sensitive waste fluid collector support(s) described above, hemoglobin concentration estimation means for estimating hemoglobin concentration in waste fluid and producing a signal indicative of estimated hemoglobin concentration in waste fluid. In such embodiments, computing means are coupled to the fluid source weight signal, to the waste fluid collector weight signal, and to the hemoglobin concentration signal for calculating an estimated fluid source flow rate, an estimated waste fluid flow rate, an estimated blood loss flow rate, a corrected waste fluid flow rate equal to the estimated waste fluid flow rate minus the estimated blood loss flow rate, and an estimated fluid absorption rate equal to the estimated fluid source flow rate minus the corrected waste fluid flow rate, and for producing first and second display signals indicative of the estimated fluid absorption rate and the estimated blood loss flow rate respectively. Display means are coupled to the computing means for transducing for human observation the fluid absorption rate display signal and the blood loss flow rate display signal.

Surgical fluid monitors and surgical fluid and blood loss monitors as described above may comprise, in place of weight-sensitive fluid source supports and/or weight-sensitive waste fluid collector supports, at least one fluid source comprising a direct-reading fluid flow rate meter and producing a signal indicative of fluid source flow rate, and/or at least one waste fluid collector comprising a direct-reading fluid flow rate meter and producing a signal indicative of waste fluid flow rate.

The invention also comprises a method of estimating a fluid absorption rate in a surgical patient. The method comprises determining a change in weight with respect to time of a source of fluid administered to the patient to form a fluid source flow rate. Then a change in weight is determined with respect to time of a collector of waste fluid draining from the patient to form a waste fluid flow rate. Finally, the waste fluid flow rate is subtracted from the fluid source flow rate to form an estimate of a fluid absorption rate in the patient.

Alternatively, the above method may comprise determining by a direct-reading fluid flow rate meter a flow rate of a source of fluid administered to the patient to form a fluid source flow rate. After then determining by a direct-reading fluid flow rate meter a flow rate of waste fluid draining from the patient to form a waste fluid flow rate, the waste fluid flow rate is subtracted from the fluid source flow rate to form an estimate of a fluid absorption rate in the patient, as above.

The invention also comprises a method of estimating a blood loss flow rate in a surgical patient. The method comprises measuring the patient's blood hemoglobin concentration and determining a change in weight with respect to time of a collector of waste fluid draining from the patient to form a waste fluid flow rate. Hemoglobin concentration in waste fluid is estimated using hemoglobin concentration estimation means, and a hemoglobin loss flow rate is estimated by multiplying the waste fluid flow rate by the waste fluid hemoglobin concentration estimate. Finally, a blood loss flow rate for the patient is estimated by dividing the hemoglobin loss flow rate by the blood hemoglobin concentration.

Alternatively, the above method may comprise determining a flow rate from a direct-reading fluid flow rate meter (instead of from a change in weight with respect to time) for waste fluid draining from the patient to form a waste fluid flow rate.

The invention also includes a method of estimating a fluid absorption rate in a surgical patient. The method comprises measuring the patient's blood hemoglobin concentration and determining a flow rate from a direct-reading fluid flow rate meter for a source of fluid administered to the patient to form a fluid source flow rate. Then a flow rate is determined from a direct-reading fluid flow rate meter for waste fluid draining from the patient to form a waste fluid flow rate. Hemoglobin concentration in waste fluid is estimated using hemoglobin concentration estimation means, and a hemoglobin loss flow rate is estimated by multiplying the waste fluid flow rate by the waste fluid hemoglobin concentration estimate. A blood loss flow rate is then estimated for the patient by dividing the hemoglobin loss flow rate by the blood hemoglobin concentration. A corrected waste fluid flow rate is then estimated by subtracting the blood loss flow rate from the waste fluid flow rate, and a fluid absorption rate is estimated by subtracting the corrected waste fluid flow rate from the fluid source flow rate.

Alternatively, the above method can be accomplished if the determinations of source fluid and waste fluid flow rates are replaced by determining a change in weight with resectto time of a source of fluid administered to the patient to form a fluid source flow rate, and determining a change in weight with respect to time of a collector of waste fluid draining from the patient to form a waste fluid flow rate respectively.

In free-standing embodiments, the invention may (as noted above) also incorporate at least one anti-rotation device to eliminate tangling of fluid supply and drainage tubes. Certain free-standing embodiments provide an adjustable floor-mounted stand or a ball-joint mount to ensure that the main fluid support column is vertical, while other embodiments employ level sensor measurements to facilitate compensation for measurements of fluid weight made when the fluid support column is off-vertical.

As noted above, the invention may comprise one or more direct-reading fluid flow sensors and/or one or more weight-sensitive fluid source and/or fluid collector suspension or support means (for example, hooks or holders) for simultaneously suspending and/or supporting and weighing one or more fluid sources and/or collectors. Fluid containers may be weighed individually (that is, allowing individual measurement of the weight suspended from each fluid suspension hook) or collectively (that is, yielding the sum of weights suspended from a plurality of fluid suspension hooks).

Further, one or more waste fluid collectors may be simultaneously weighed, optionally in combination with one or more fluid sources. In this case, because a single weight measurement reflects the combined weight of all fluid sources and waste fluid collectors, the weights of individual sources and collectors is obtained, if desired, by removing the source or collector in question and noting the decrease in combined weight.

The invention may alternatively comprise, for example, one or more fluid source supports (preferably hooks) spaced apart from each other and from any waste irrigation fluid collector support (for example, by mounting on a wall), or source and collector supports may be mounted on a fluid support column which itself is fixed (as by welding or bolting) to a platform or equipment cart movable over the floor. The platform or cart preferably has retractable wheels or extendable legs which facilitate stable positioning in a desired floor location. Fluid source hooks mounted on a wall, for example, are necessarily inherently weight-sensitive (that is, they comprise at least one weight-sensitive element), but fluid source hooks mounted on a fluid source column may be inherently weight-sensitive, or may be weight-sensitive only in the sense that the column comprises at least one weight-sensitive element.

In use, fluid-containing bottles, plastic bags, or similar containers are suspended from a fluid source hook to hang substantially freely (that is, substantially vertically). Preferred embodiments of weight-sensitive fluid source hooks comprise one or more (preferably solid-state) force-sensitive devices, each producing a signal indicative of the weight applied to a single hook. Alternatively, a single force-sensitive device may also be employed (for example, within the fluid support column) to produce a signal indicative of the weight applied to all column-supported fluid source hooks collectively. In either of the latter two cases, a separate force-sensitive device would preferably be employed to produce a signal indicative of the weight of waste fluid collected, either as a separate signal or combined with the weight of fluid sources supported by a fluid support column.

For convenience, waste fluid will commonly be distributed into a plurality of collection containers which will be weighed collectively. In a preferred embodiment, the collection containers are suspended from a fluid support column and all fluid sources (including irrigation fluid sources and intravenous fluid sources) are suspended from weight-sensitive hooks. When combined with apparatus to provide the above-described independent determination of blood loss flow rate, such a system can provide information allowing substantially total fluid management for a surgical patient. Additionally, opportunities for fault detection in the fluid source and collection pathways will be significantly greater than those available in preset systems.

In preferred embodiments of the invention, each force-sensitive device comprises a solid-state load cell (comprising e.g., a piezoelectric or stain gage force sensor). Fluid support means thus produce a source weight signal indicative of fluid source weight, the signal eventually being coupled to computing means by coupling means which include one or more insulated electrical conductors and/or wireless means (including a radio transmitter and receiver or, preferably, an infrared transmitter and receiver). In the latter case, the infrared transmitter for the signal indicative of a fluid source weight may preferably be battery-powered.

In certain embodiments, the force-sensitive device does not sense the full weight of fluid supported by the fluid support means. This may occur, for example, if a platform-mounted fluid support column is placed on an uneven or sloping floor where the platform would not be substantially level. If the non-level platform causes the fluid support column to be non-vertical, then a component of the fluid weight vector will not be coaxial with the column. The non-coaxial weight vector may then be resolved into an axial component (creating a reduced axial compressive stress in the column) and a transverse component (creating transverse or shear stress in the column). The reduced axial compressive stress is obtained by multiplying the axial compressive stress that would be present if the column were vertical by the cosine of the angular deviation of the column from vertical. Since the force-sensitive device responds substantially to axial stress, the indicated weight on the pole will always be less than the true weight unless the pole is vertical. For small deviations from vertical, the errors in indicated weight will be relatively small, but they will be systematic (i.e., always increasing as additional fluid sources are supported by the column).

The present invention preferably comprises methods and apparatus to eliminate and/or compensate for the above verticality errors. For example, if the platform-mounted column is configured with a verticality adjustment, the pole can be made substantially vertical even if the platform is not level. In preferred embodiments, the verticality adjustment comprises a ball-joint column mount in which the column can be positioned vertically either manually or automatically, being held in place with a plurality of manually or automatically adjusted mechanical stops (such as screws). Such a ball-joint support may be relatively close to the column platform at the lower end of the pole, or sufficiently elevated so that the center of gravity of the column, force-sensitive device, fluid source(s) and waste fluid container(s) is lower than the ball-joint support point. In the latter configuration, the column will be free to behave as a pendulum and will maintain a substantially vertical orientation within its range of motion in the absence of significant eccentric vertical loads.

Yet another approach to the verticality problem with a platform-mounted column is to allow the column to maintain a non-vertical position while measuring the degree of deviation from the vertical and using the measured deviation and reduced axial force to calculate the true weight of one or more fluid sources and/or waste fluid containers.

Waste fluid containers have a relatively large capacity (preferably about 3 fluid liters) in certain embodiments to obviate frequent emptying of the container during a surgical procedure. Because each such container weighs more than 3 kilograms when full, even small verticality errors may cause clinically significant errors in fluid volume estimates. The container is substantially sealable and has a vacuum port (to be optionally connected to a vacuum pump) to facilitate establishment of a partial vacuum within the container which will tend to draw irrigation fluid in through the port(s) provided in the container, allowing effective scavenging of waste irrigation fluid from a surgical site (as by a surgical sucker).

A display signal (preferably generated by a programmable digital computer) is transmitted to display means, for transducing the display signal for human observation. The display means may comprise a computer screen and/or a digital readout. In preferred embodiments, the computing means may transmit the display signal in, for example, ASCII code to a commercially available digital readout device capable of decoding and displaying ASCII-coded signals. Several such devices are available through commercial electronics parts distributors and, while not further described herein, are well-known to those skilled in the art. Note that intermediate values of variables obtained in the course of producing the calculated fluid absorbed value may also be displayed as desired.

As noted above, preferred embodiments of the surgical fluid and blood loss monitor include a vacuum connection to the fluid collector container to facilitate optional maintenance of a partial vacuum within the container in use. The partial vacuum, in turn, facilitates entry of waste irrigation fluid into the container from other sources in addition to the endoscope drain. Thus, while the surgical fluid and blood loss monitor is particularly adapted for use with endoscopic surgical procedures in substantially closed body cavities, it may also be used with partially or substantially open surgical procedures wherein waste irrigation fluid and blood are substantially completely collected. In such cases, the collector may receive waste fluid from a floor sump or fluid-trapping floor mat, or a drain configured to recover irrigation fluid which splashes on the operating table or which emerges from an operative site (for example, a vagina or urethra) with the patient in the lithotomy position). Additionally, the fluid collector container may comprise a filter or strainer intended to separate small pieces of tissue from one or more incoming streams of waste irrigation fluid, as well as a bunghole and/or stopcock to facilitate emptying the container. Note that in operations involving very vascular tissues (as, for example, the uterine lining), fluid absorption rather than blood loss may be the predominant hemodynamic variable of clinical interest.

Total fluid flow per measurement period (that is, fluid flow rate) may be determined manually or substantially automatically using flow rate meter signal output integrated over the measurement period, or weight measurement means or volume measurement means applied at the beginning and end of a measurement period. Volume measurement means include, for example, measurement of volume change in a fluid container (as by a floating level sensor or a light beam interruption level detector) or measurement of volume moving past a fixed point in a fluid line (as by a positive-displacement pump). Weight measurement means include measurement of change in weight of a (suspended or supported) fluid container (as an irrigation fluid source bag hanging from a weight-sensitive hook or a waste fluid collector placed in a weight-sensitive holder).

Note that when it is desired to integrate a fluid flow rate which is a piecewise continuous function (as when flow rate is calculated periodically from a series of discrete fluid weight and/or volume measurements over time), measurement time intervals for the integration will preferably be identical to the intervals between the weight and/or volume measurements. Such predetermined intervals are preferably established by programming a digital computer prior to the start of surgery. The existence of substantially steady-state fluid flow conditions during these measurement time intervals is then preferably independently verified (as by an independent direct-reading flow rate meter in the respective fluid stream). Artifacts in the desired steady-state irrigation fluid and waste irrigation flow data may cause erroneous flow rate estimates. Such disturbances are preferably removed by processes analogous to the low-pass filtering described above as optional in the integration means, or they may be detected and compensated or flagged by error handling means which comprise a separate stored program coupled as above with a digital computer within the computing means.

Compensation of fluid volume flow rates for artifacts may include elimination of one or more spurious data points and/or lengthening of the measurement time period as needed to effectively smooth the fluid flow rates measured over the period. Data points which are apparently due to malfunction or artifact (zero indicated flow or brief but large amplitude peaks and dips in flow rate, for example) are preferably flagged on a display to indicate to an operator a possible system fault such as a kinked fluid line, an empty source container, a fluid line disconnect, or a full waste fluid collection vessel. On the other hand, the need to terminate a measurement interval (and prepare to start another) might be indicated, for example, by an abrupt indicated change in either source fluid or waste irrigation fluid flow rates. This might be caused by the opening or closing of an endoscope valve, the temporary kinking of a fluid source or collector line, or the abrupt changing of pressure on the body cavity (as by a surgical assistant leaning on the patient).

Preferred embodiments of the invention may also include error handling means which can detect the presence or absence of substantially steady-state flow conditions for source and waste irrigation fluid over a fluid flow measurement period (or any portion thereof). Error handling means preferably detect abrupt changes in source and/or collector fluid flow rates through comparison of actual and/or estimated fluid flow rate changes with predetermined limits on (calculated and/or measured) flow rate change during successive flow measurement periods or within a single flow measurement period for source and/or collector fluid. Additionally or in lieu of the comparison of fluid flow rate changes with predetermined limits, error handling means may compare endoscopic fluid system pressure changes (as, for example, changes in fluid pressure within the body cavity into which the endoscope is inserted) with predetermined limits established for such pressure changes during successive flow measurement periods or within a single flow measurement period.

Comparison of changes in fluid flow rates and/or changes in fluid pressure with predetermined limits on the respective measurements may be accomplished manually, but is preferably automatically performed by computing means comprising a programmable digital computer. Analogously, calculation and/or estimation of fluid flow rates may be accomplished manually, but is preferably automatically performed by computing means comprising a programmed digital computer. Inherent in the latter embodiments of the invention is a digital computer comprising input/output interfaces (including analog-to-digital converters and digital-to-analog converters well known to those skilled in the art) for sensors for fluid pressure and/or fluid flow and/or fluid weight and/or fluid volume, together with memory means (such as a magnetic disk or random access memory) for storing data from the sensor(s) and at least one computer program, computer input means (such as a keyboard) for entering into the memory means computer instructions and data such as limit values, display means (such as a liquid crystal screen or analogous visual display) for displaying computer instructions, data, and/or calculated values, and alarm means (such as a flashing portion of a visual display or an audio alarm buzzer) for indicating that one or more predetermined limits have been exceeded.

FIGS. 1–5 schematically illustrate preferred embodiments of portions of a surgical fluid monitor comprising verticality compensation means and anti-rotation devices. The fluid support column 70,70' may comprise a plurality of passive fluid source hooks 50 (that is, hooks without inherent weight-sensing capability). Alternatively, column 70,70' can have no fluid source hooks at all, or one or more weight-sensing hooks as schematically illustrated in FIGS. 12A–E (that is, hooks comprising one or more force-sensitive devices such as a piezoelectric sensor (load cell) 64 or a strain gage sensor 62). The height of fluid source hooks, if present, may be manually adjusted by sliding member 70' in or out of member 70 and temporarily fixing the height of column 70,70' with thumb screw 71.

Figure 2:
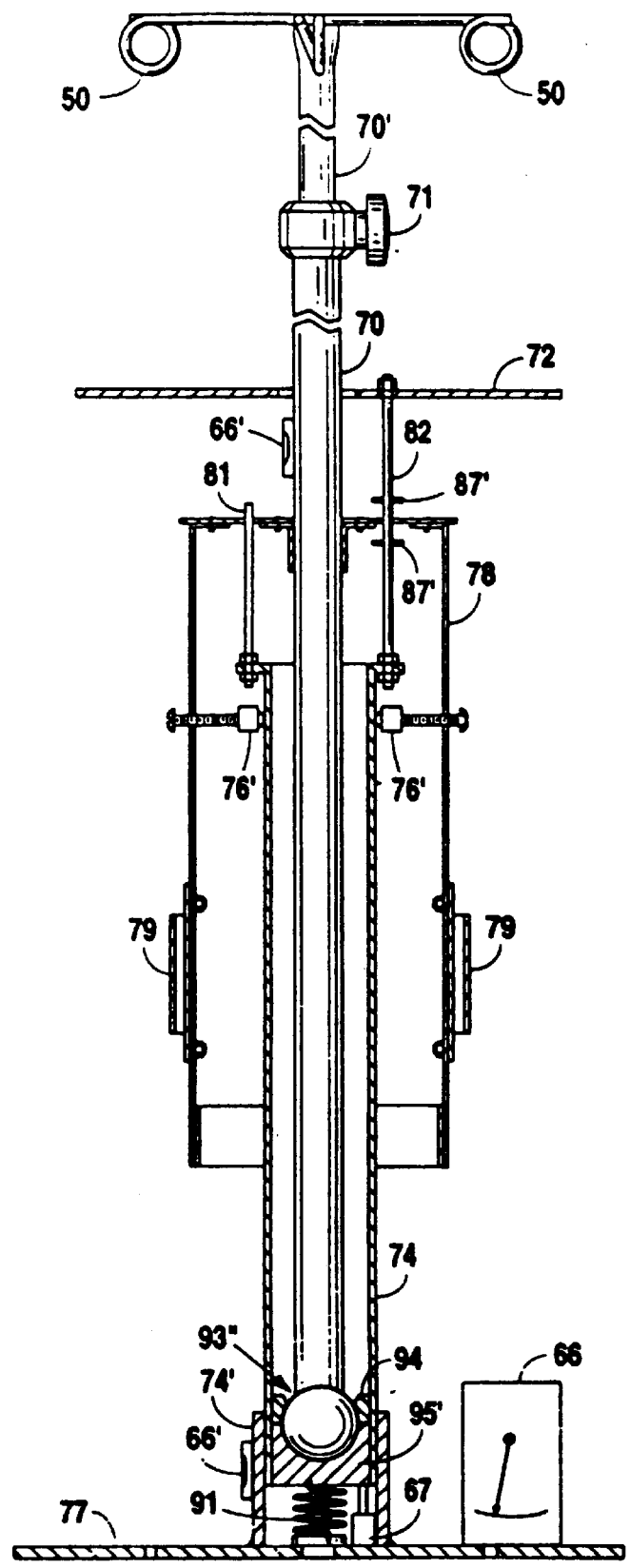
FIG. 2 schematically illustrates a preferred arrangement for source fluid supports and fluid collector supports on a ball-joint fluid support column with verticality adjustment which bears on a single weight-sensitive element.
Figure 3:
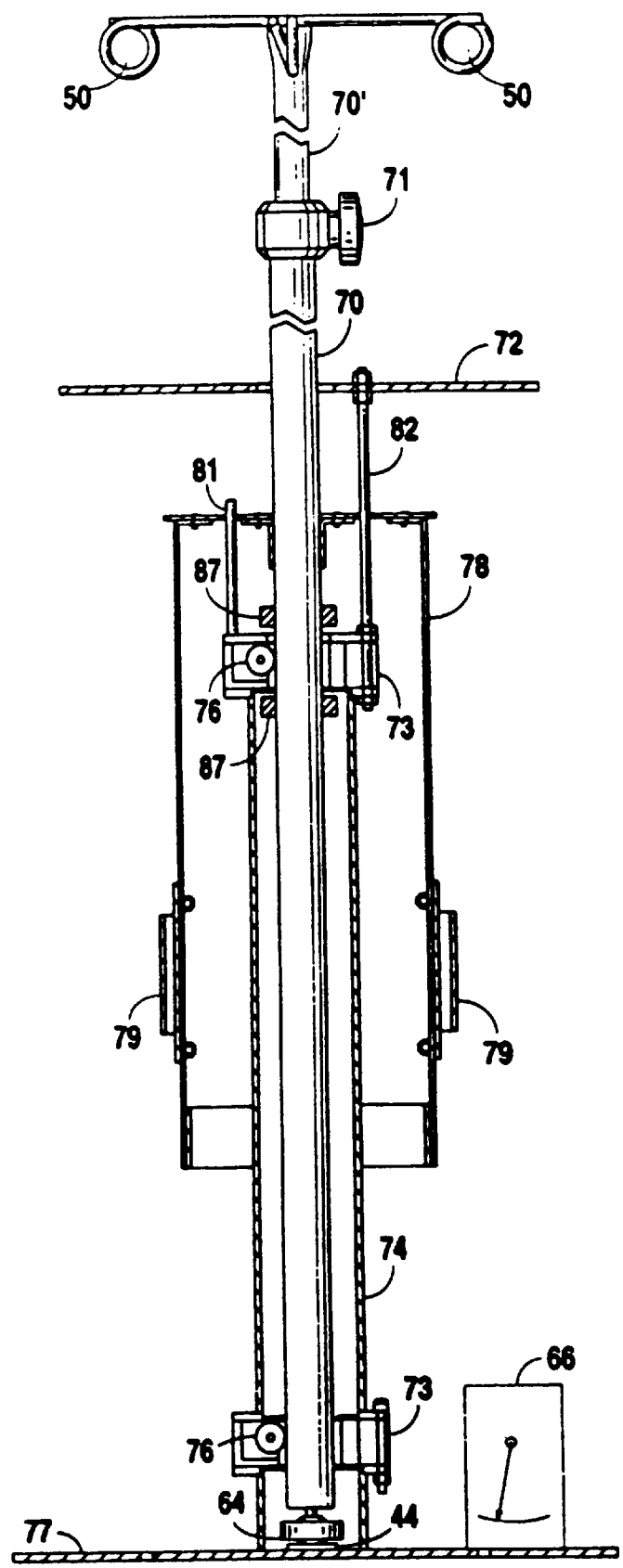
FIG. 3 schematically illustrate: a preferred arrangement for source fluid supports and fluid collector supports on a fluid support column having a verticality sensor and bearing on a single weight-sensitive element.
Figure 4:
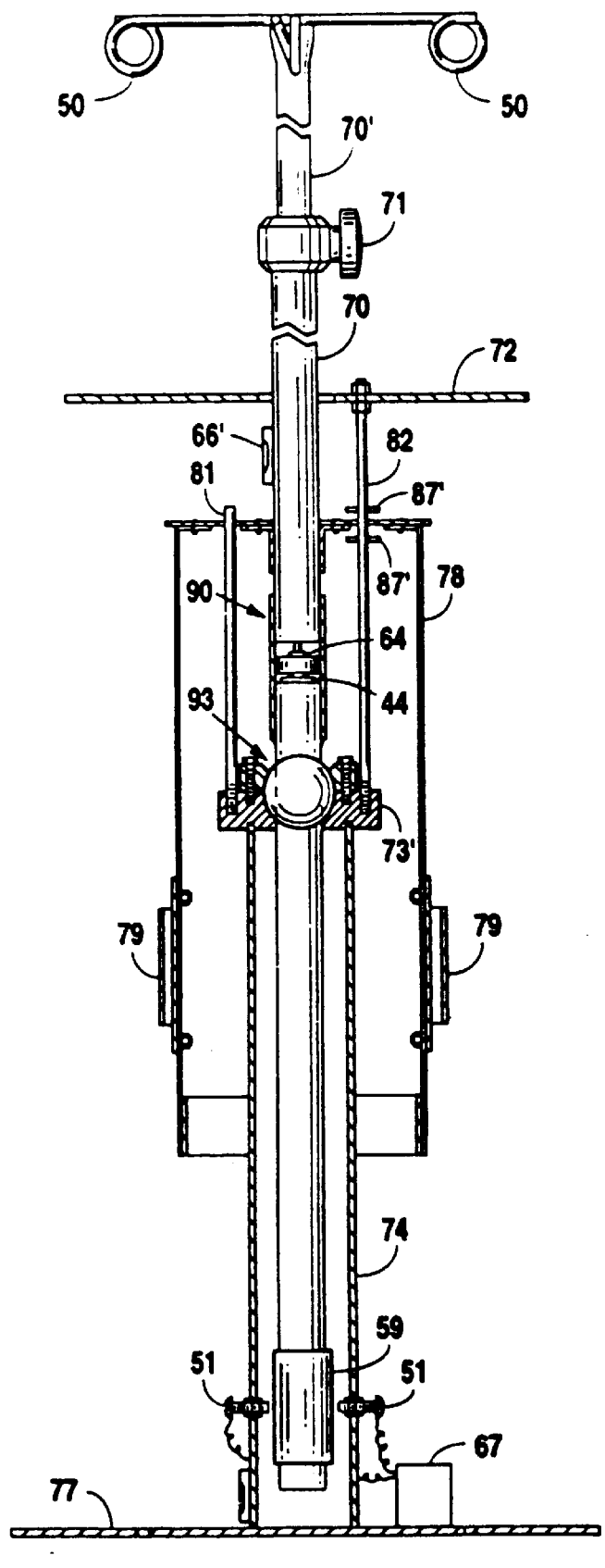
FIG. 4 schematcally illustrates a preferred arrangement for source fluid supports and fluid collector supports on a ball-joint supported pendulous fluid support column bearing on a single weight sensitive element.
Figure 5:
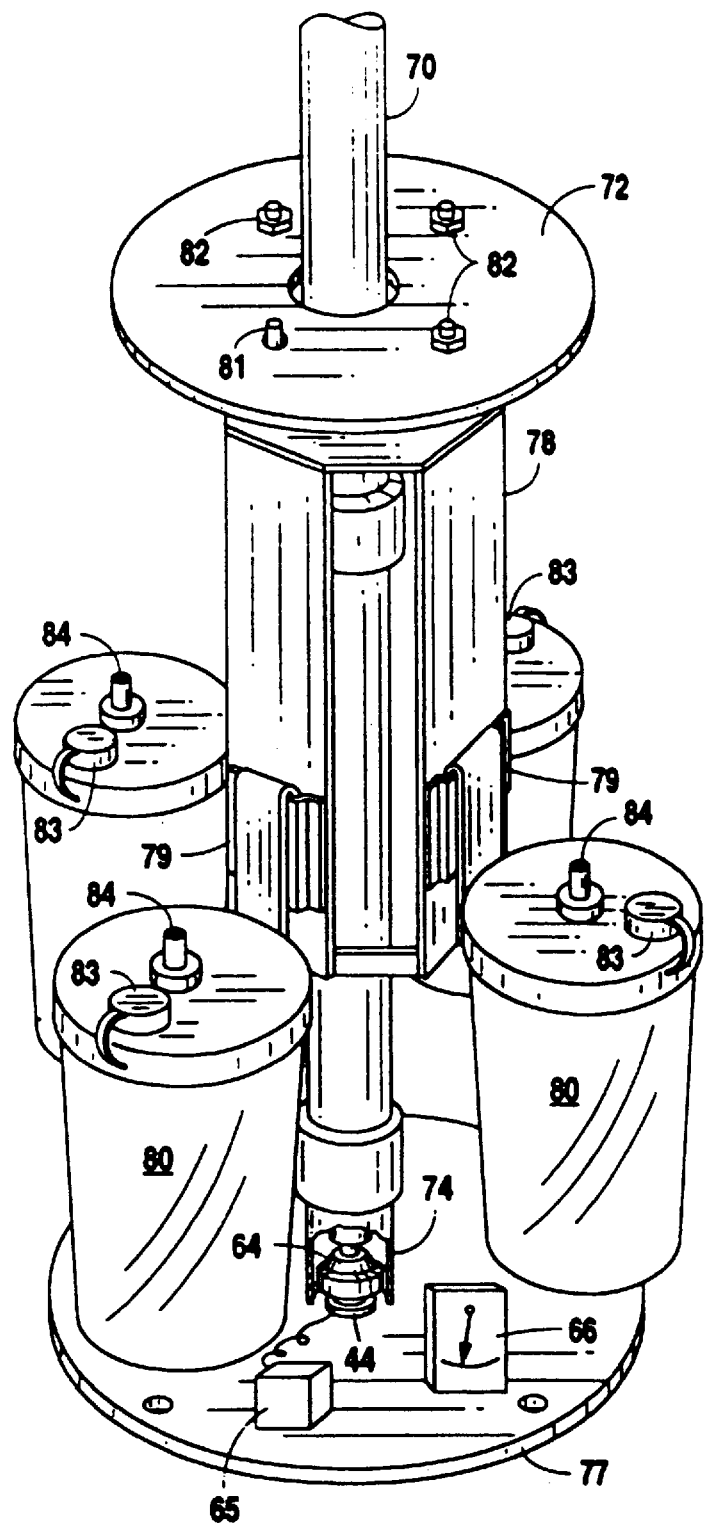
FIG. 5 schematially illustrate a preferred arrangement for fluid collector supports on a fluid support column bearing on a single weight sensitive element.
Figure 7:
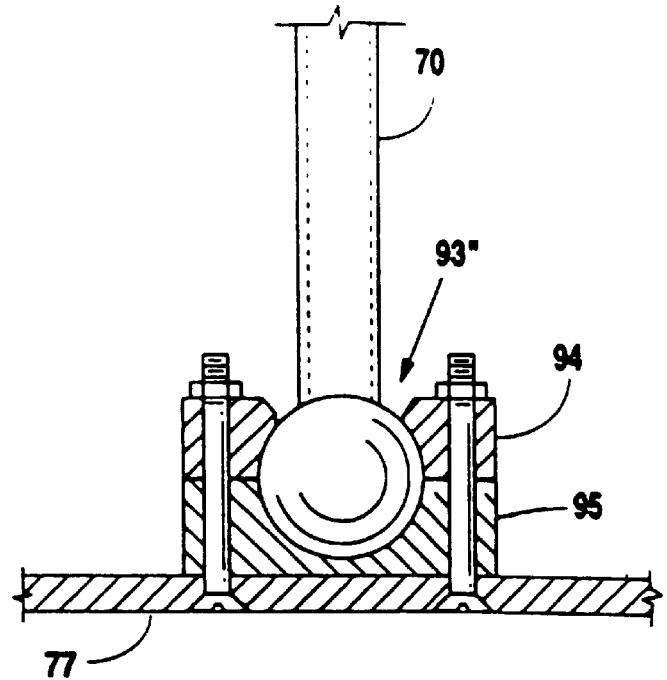
FIG. 7 schematically illustrates a ball-joint support for a fluid support column.

In each of the FIGS. 1–5, a platform-mounted support sleeve 74 is firmly fixed to a base plate 77 (as by welding), with base plate 77 intended to rest directly on a floor or on (retractable or lockable) casters or legs (not shown). Optional shelf 72 is coupled (as by stand-off bolts) to support sleeve 74, and shelf 72 does not contact column 70,70' in use. Shelf 72, when present, is supported by standoff bolts 82 which, like anti-rotation pin 81, are fixed to support sleeve 74 through bearing block 73 (FIGS. 1 and 3), through a flange of sleeve 74 (FIG. 2), or ball-joint socket block 73' (FIG. 4). Block 73' sleeves part of the purpose of bearing block 73 (capping sleeve 74 and anchoring anti-rotation pin 81 and stand-off bolts 82) as well as providing the lower portion of ball-joint 93. Wherever ball-joint sockets are found in the illustrated embodiments (see, for example, FIGS. 2 and 7, ball-joints 93' and 93" respectively), the ball is retained in the socket bearing (95' and 95 respectively in FIGS. 2 and 7) by a ball retainer 94. Note that the ball-joint socket of FIG. 7 illustrates a portion of an embodiment wherein a terminal ball-joint 93" is directly mounted on base plate 77. The configuration of FIG. 7 contemplates use of one or more in-line force-sensitive assemblies 90 in fluid support column 70,70' (see FIG. 4), although the entire embodiment is not shown.

Figure 8:
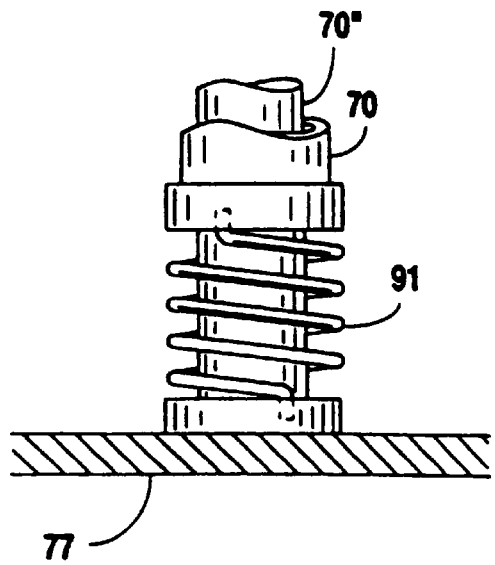
FIG. 8 schematically illustrates a spring support for a fluid support column.

Anti-rotation pin 81 passes through an enlarged hole in collector support frame 78, thereby preventing frame 78 and column 70,70' from rotating excessively with respect to pin 81, support sleeve 74 and base plate 77. Additional anti-rotation devices schematically illustrated in the drawings include the optional in-line force-sensitive assembly 90 (comprising load cell 64, in-line sleeve 89, spline 88 and optional shock absorber 44 of resilient material such as rubber or other polymer), and the anti-rotation support spring 91 (FIGS. 1, 2 and 8). Note that certain configurations of load cell 64 which are securely coupled (as by bonding or gluing) to optional shock absorber 44 comprise anti-rotation devices when the load cell 64 and shock absorber 44 are themselves securely coupled to the respective contacting parts of the surgical fluid and tissue loss monitor. One such configuration is shown in FIG. 3, in which the anti-rotation pin 81 serves to augment the anti-rotation function of the load cell-shock absorber combination 66,44; in such a case, pin 81 may be eliminated entirely in certain embodiments without loss of the desired anti-rotation function. Note also that support spring 91 may be used without an internal guide (see FIG. 2), or with an internal guide 70" (see FIG. 8) over which it slides and which will tend to stabilize spring 91.

Collector support frame 78 is supported by column 70,70' and in turn supports waste fluid collectors 80 via collector brackets 79. Waste fluid enters collectors 80 via inlet ports 83 (capped when not in use) assisted by vacuum applied via vacuum ports 84. The weight of fluid collectors 80 is carried by support frame 78, which is itself supported by fluid support column 70,70'. Column 70,70', in turn, is supported by at least one weight-sensitive device. In FIGS. 1 and 2, the weight-sensitive device comprises spring 91 and means to measure spring 91 compression and/or expansion (for example, a linear variable differential transformer (LVDT) 67 coupled around spring 91 substantially as shown). In FIGS. 3 and 4, the weight-sensitive device comprises a load cell 64 (the load cell itself comprising, for example, a piezoelectric load sensor). Note that travel of fluid support column 70,70' which compresses or expands spring 91 is preferably limited to prevent damage to spring 91 and/or to LVDT 67. This travel limitation may, for example, be via stop rings (not shown) adjustably fixed (as by set screws) to member 70 above and below (and proximate to) shelf 72. Shelf 72 would then contact the upper or lower stop ring at the respective limits of travel. Analogously, travel limitation to prevent damage to load cell 64 may be via stop pins (not shown) adjustably fixed to stand-off bolts 82 as through one of a plurality of transverse holes in bolts 82 above and below (and proximate to) support frame 78 where bolts 82 pass through support frame 78. Support frame 78 would then contact the upper or lower stop pin at the respective limits of travel.

Figure 6:
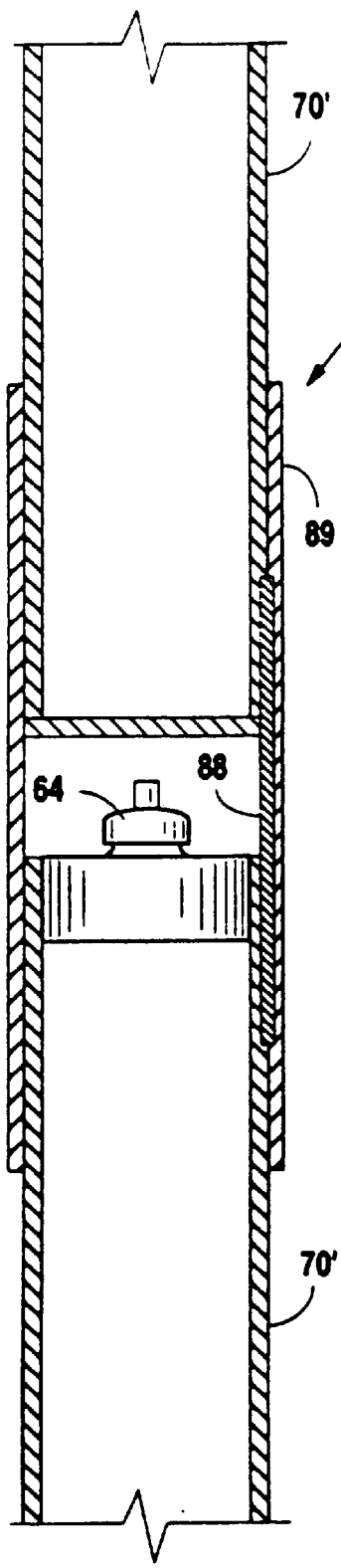
FIG. 6 schematically illustrates an in-line force-sensitive device.

Note that travel of fluid support column 70,70' as described above is facilitated by one or more sleeve or roller bearings in the schematically illustrated embodiments of FIGS. 1–3 (roller bearings 76,76') and of FIG. 2 (the sleeve bearing formed by ball-joint 93' sliding within support sleeve 74), and of FIG. 6 (the sleeve bearing formed by the upper portion of member 70' of in-line force-sensing assembly 90 sliding within splined sleeve 89 guided by spline 88). Note that the lower portion of member 70' (as in FIG. 6) would preferably be firmly fixed to the lower end of splined sleeve 89 as by screw threads or an interference Fluid support column 70,70' may be adjusted to be vertical or may be allowed to tilt off-vertical in embodiments with a sufficiently large base plate 77 to prevent significant instability. FIGS. 2 and 4 schematically illustrate two verticality compensation means in which fluid support column 70,70' is rotated within a ball joint 93',93 to achieve verticality as indicated by verticality sensor 66" on the column 70,70'. Verticality sensor 66' is a column-mounted version of verticality sensor 66 which is schematically shown as indicating tilt of base plate 77 in FIGS. 1–3 and 5. Sensors 66,66' may be bulls-eye bubble levels or analogous pendulous sensors well-known in the art for measuring tilt about any horizontal axis (the sensors preferably producing an electrical signal indicative of such tilt).

Fluid support column 70,70' may be adjusted to be vertical by rotation about an end-mounted ball joint 93',93" with thumbscrew-mounted bearings 76', or it may be allowed to hang vertically (pendulously) while supported in ball joint 93. In the latter case, a sufficiently heavy weight 59 must be placed below ball joint 93 to insure that the center of gravity of the entire fluid support column 70,70' (including all fluid sources and waste fluid containers) is below ball joint 93. Note that for the pendulous column, eccentric loading will tend to cause an off-vertical condition. This condition can be indicated by the verticality sensor 66' or by contact of the pendulous fluid support column with previously adjusted thumbscrew-mounted electrical switch contacts 51 which can be made to light a bulb, ring a bell or otherwise signal an alarm in junction box 67.

For the pendulous fluid support column of FIG. 4 having an in-line force-sensitive assembly 90, the output signal of force-sensitive device (load cell) 64 includes the true weight of the source fluids and waste fluids supported by the (vertical) column, while the output signal of load cell 64 in FIG. 3 or of the linear variable differential transformer 67 in FIGS. 1 or 2 (which measures weight-induced compression of anti-rotation support spring 91) will include only a (potentially) reduced indication of the true weight of supported fluid (that is, the true supported weight multiplied by the cosine of the off-vertical angle of support sleeve 74. When using the embodiments of FIGS. 1–3, the true weight may be obtained by measuring the off-vertical tilt of support sleeve 74 with level sensor 66 and dividing the indicated weight by the cosine of the off-vertical tilt angle.

Thus, verticality compensation means can provide true indications of changes in the fluid weights supported by fluid support column 70,70' by making the column (and the sensitive axis of the force-sensitive device) substantially vertical, or by measuring the degree of off-vertical tilt in the column and using that information to calculate true weights from indicated weight values.

Figure 11:
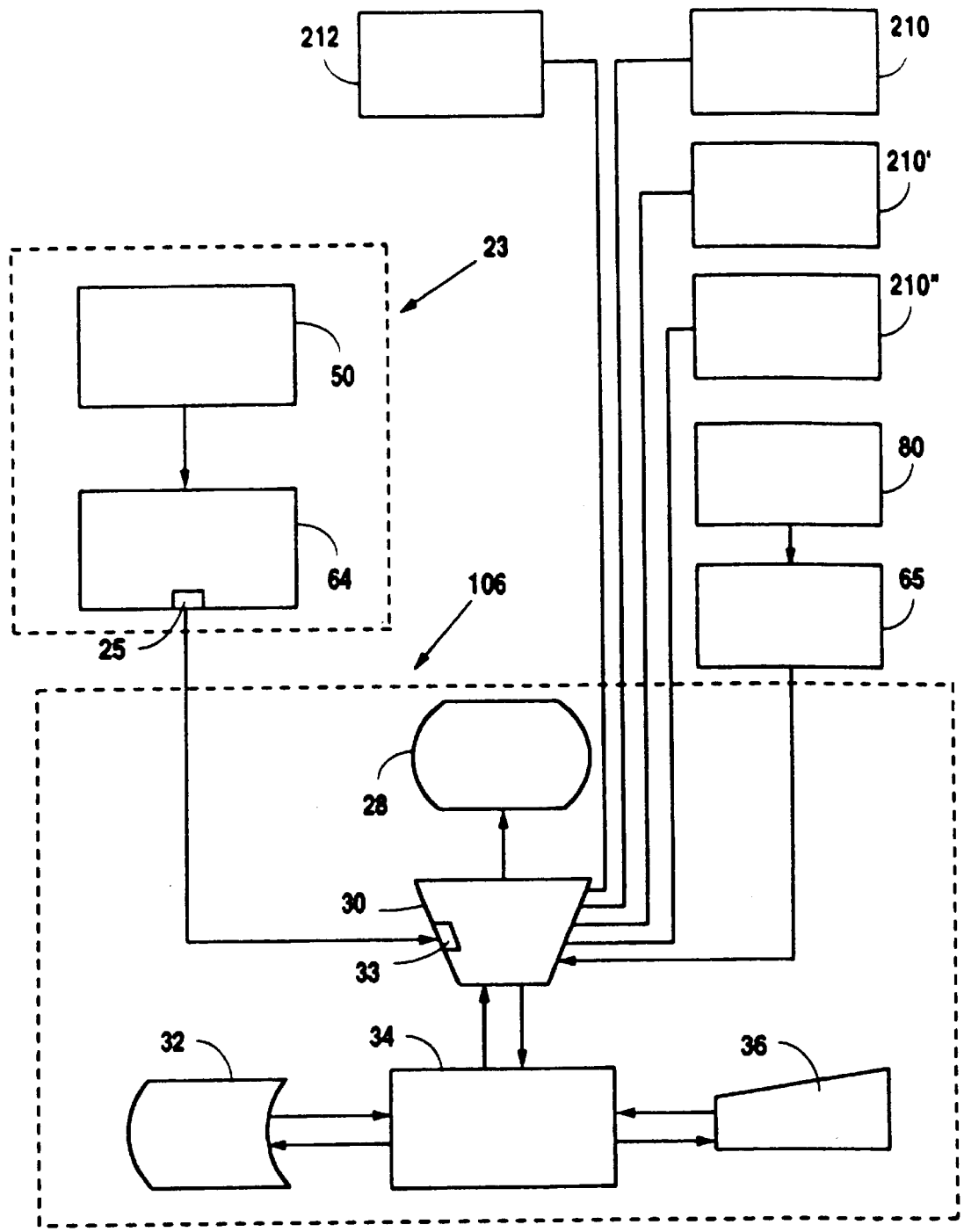
FIG. 11 schematically illustrates the flow of signals in a preferred embodiment of the invention.

In certain embodiments, the above measurements and calculations can be made automatically according to a predetermined program. Referring to FIG. 11, the signal flow in a preferred embodiment of the invention involving separate measurement of source and waste fluid weights can be seen to originate in part from the weight-sensitive fluid support means 23 which comprises (see FIGS. 12A–E, for example) a source fluid support hook 50 coupled to a weight-sensitive device 64 (e.g., a solid-state load cell). Signal flow in FIG. 11 also originates from fluid collectors 80 acting on an irrigation fluid collector weight sensor combination 64,65 (comprising load cell 64 and matched commercially-available signal conditioning means 65, as in FIG. 5). Signal conditioning means may be used, for example, to change the form of the signal (as by modulating a carrier waveform) or change an electrical characteristic (like the impedance of the signal source). Note that in an alternative embodiment, one or more fluid collectors 80 may also be placed on a commercially available electronic scale (not shown) comparable to those used for weighing patients and having a signal output analogous to that of weight sensor combination 64,65 (see FIG. 5). Fluid source weight signals from weight-sensitive device (load cell) 64 are directed by transducer coupling means to the input-output section 30 of computing means 106 (see FIG. 11). In addition to input-output section 30, computing means 106 comprises memory means 32, processor means 34, display means 28 and manually-actuated input means 36.

Input-output section 30 in preferred embodiments may be configured to receive signals transmitted by insulated electrical conductor(s) and/or to receive wireless (e.g., radio or infrared) signals from wireless transmitter means 25 with wireless receiver means 33. Transducer coupling means herein include, for example, one or more insulated electrical conductors and/or wireless transmitter means/receiver means combinations 25,33. Wireless transmitter means 25 may comprise, e.g., infrared transmitter 63 is FIGS. 12A, 12B. Flow of signals through input-output means 30 to processor means 34 and memory means 32 is controlled by processor means 34 using instructions (that is, a program) stored in memory means 32 and/or instructions from manually-actuated input means 36. Processor means 34 includes a time base to facilitate calculation of flow rates based on changes in weight or volume of fluid per unit time. Depending on the embodiment of the invention considered, processor means 34 preferably computes rate of fluid absorption, volume of fluid absorbed, and the rate of blood loss and volume of blood lost according to methods analogous to or substantially identical to those described herein, directing the respective signals representing the calculated values through input-output means 30 to display means 28.

Memory means 32 may comprise, for example, magnetic tape, magnetic disks, or non-magnetic solid-state devices (e.g., optoelectronic memory or solid state switches). Manually- actuated input means 36 may comprise, for example, magnetic cards, punched cards, paper or magnetic tape, a key board, or one or more switches. Processor means 34 and input-output means 30 may take the form, in preferred embodiments, of the analogous sections of a personal computer. However, display means 28 may comprise in addition to or in place of a computer display screen a digital readout device and/or an auditory indication of the calculated fluid absorbed value and/or auditory signals indicating when the calculated value has exceeded a limit previously stored in memory means 32 or entered into processor means 34 through manually-actuated input means 36.

Figure 12A:
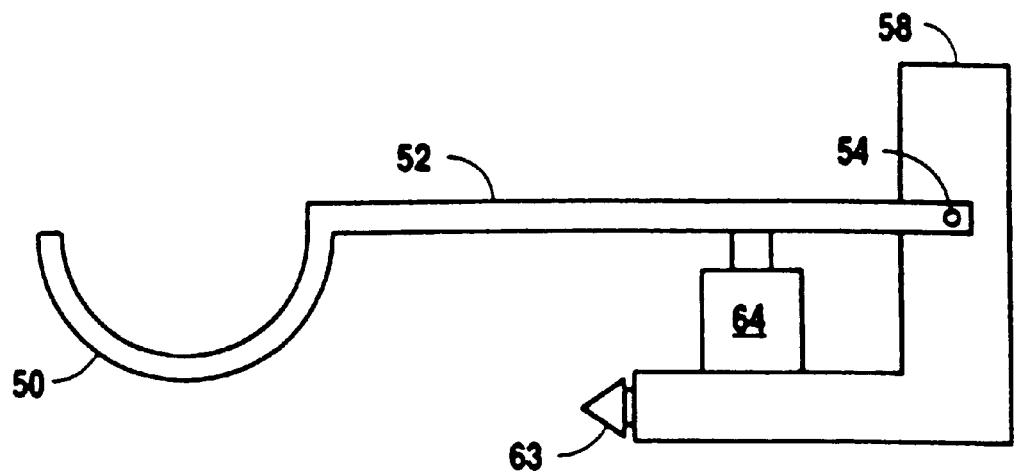
FIGS. 12A–E schematically illustrate alternative preferred embodiments of weight-sensitive fluid supports.

FIGS. 12A–E schematically illustrate examples of alternative preferred embodiments for weight-sensitive fluid supports. In FIGS. 12A–D, hook 50 is intended to suspend a fluid container (e.g., a plastic bag or a bottle made of glass or plastic). Hook support arms 52,52" are preferably substantially rigid, being pivotally coupled through pivot bearing 53,54 to support arm frames 58,60 respectively. Each support arm 52,52" is supported at an intermediate point of its length by a force-sensitive device (load cell) 64 which is preferably a solid-state load cell. Note that pivot shaft 53 (see FIG. 12C) preferably acts simultaneously to couple support arm 52" to support arm frame 60 and also to limit the motion of a substantially parallel (but oppositely oriented) support arm 52". By its position within a substantially elongated oversized slot 55 in the oppositely oriented support arm 52", pivot shaft 53 allows only limited upward motion of the oppositely oriented support are 52", but does not interfere with the support arm's bearing on load cell 64. Note that in the configuration illustrated in FIGS. 12C–E, each support arm 52" bears eccentrically on load cell 64. This is in contrast to the condition of substantially concentric loading of load cell 64 by a single support arm 52 as illustrated in FIG. 12A. The degree of eccentric load cell loading by substantially parallel and oppositely oriented support arms 52" can be reduced by reducing the arm thickness and/or the spacing between portions of substantially parallel arms 52" proximate to notches 57,57' because it is these proximate portions which bear on load cell 64. Note that if it is desirable to ensure individual contact of all support arms 52" with load cell 64 in the embodiment of FIG. 12C, notches 57,57' must be sufficiently deep to avoid contact between any two notches 57,57'. In certain preferred embodiments, however, individual support arm contact with load cell 64 is not required, and notches 57,57' can be more shallow so that each notch 57 bears on at least one notch 57' simultaneously with or instead of bearing on load cell 64. In any case, support arms 52,52',52" should be substantially horizontal to ensure that signals from load cell 64 accurately indicate the weight suspended from any arm. For non-horizontal support arms 52,52',52", as caused by tilt of the support column 70,70', a corrected weight can be calculated by dividing the indicated weight by the cosine of each arm's angular deviation from the horizontal, analogous to the correction described above related to verticality compensation means. Note that accurate measurement of the deviation of each arm from the horizontal requires a sensor 66,66' oriented to provide accurate measurement of tilt along the longitudinal axis of the arm in question. To further enhance accuracy, it is preferred that load cell 64 comprise means (for example, hydraulic coupling) to ensure that eccentrically applied loads are substantially accurately represented in a signal indicative of the load applied to the load cell.

Figure 12B:
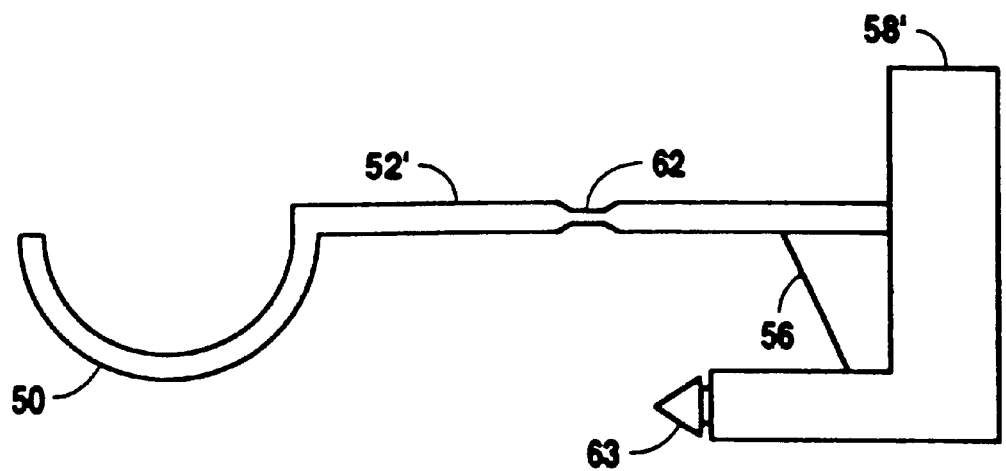
Figure 12C:
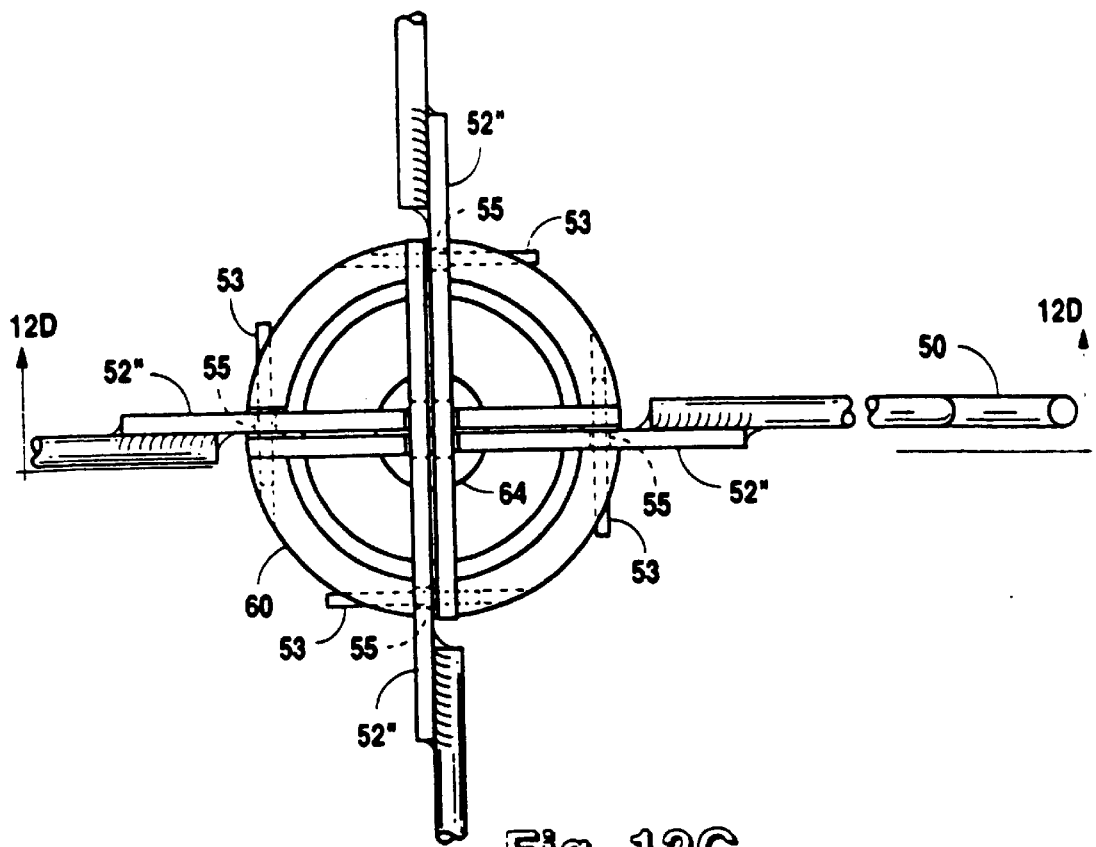
Figure 12D:
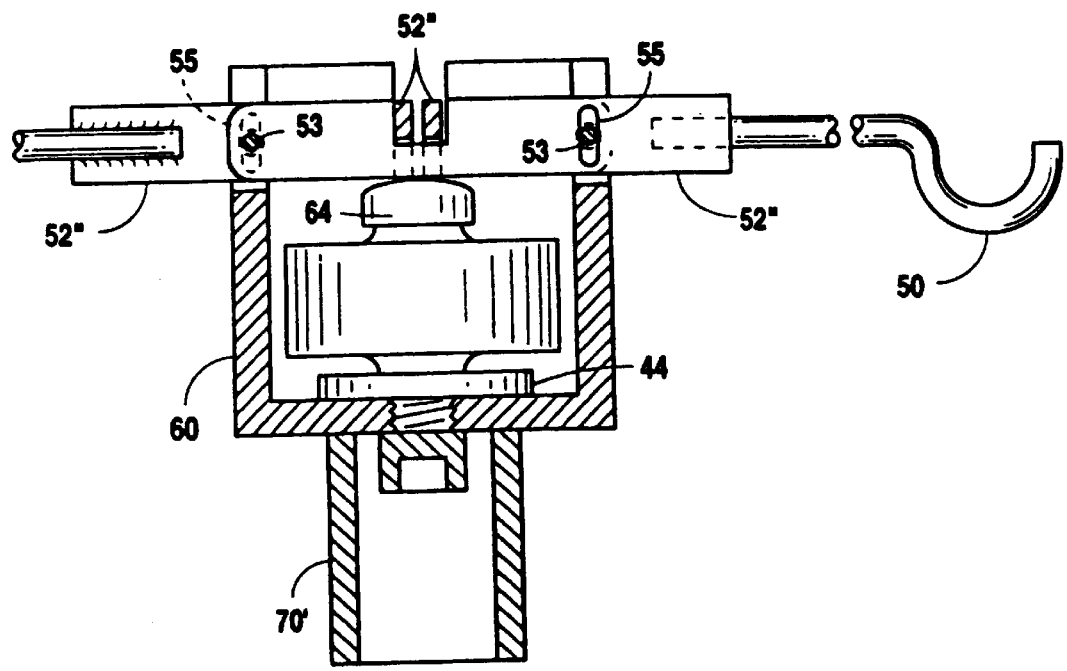
Figure 12E:
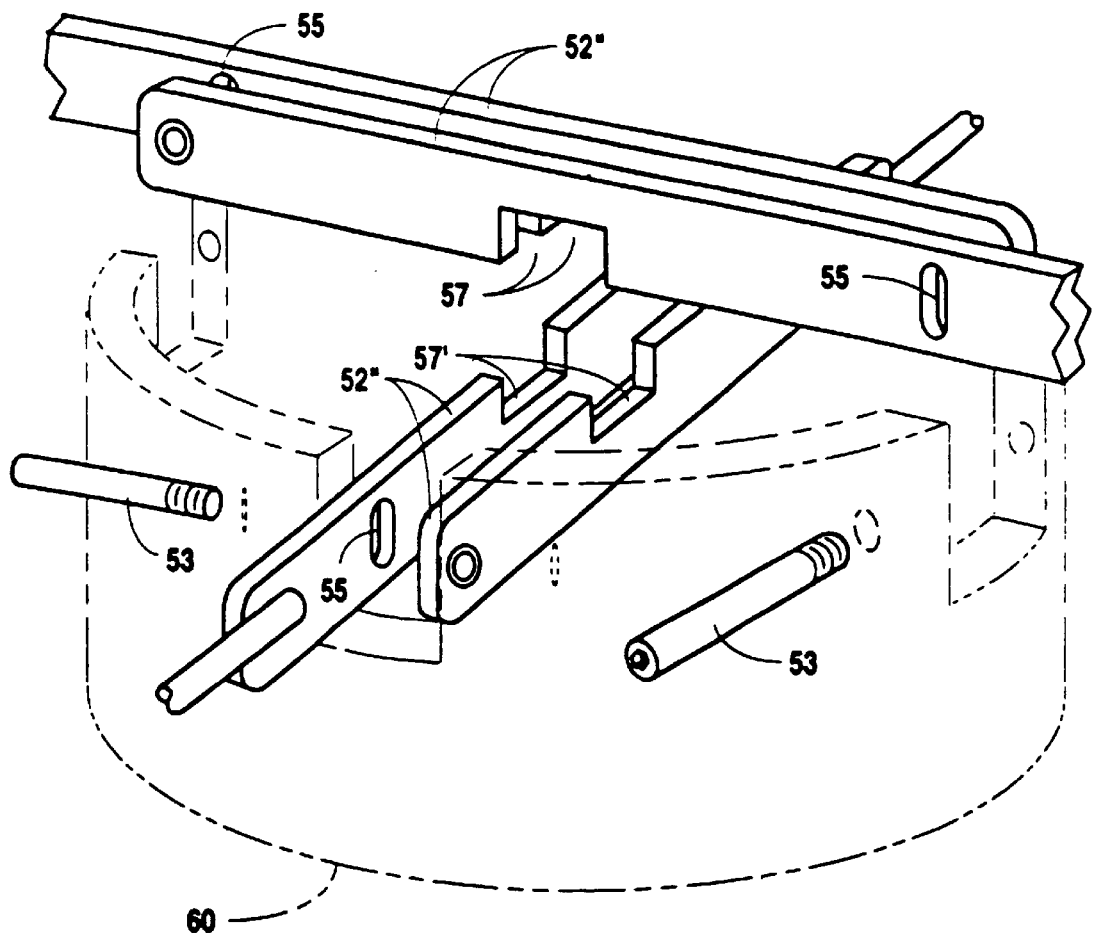

In FIG. 12B, hook support arm 52' is preferably substantially rigidly coupled to support arm frame 58' and angle brace 56, but may deflect under load slightly due to bending which is sensed by strain gage 62. Either force-sensitive device (load cell) 64 or strain gage 62 may be chosen in preferred embodiments to produce a source weight signal indicative of fluid source weight.

Support arm frames 58,58' can be mounted on a wall, pole, cabinet, rack, or other suitable surface, with signals from load cell 64 and/or strain gage 62 being preferably being coupled to input-output section 30 of computing means 106 through one or more wires or through infrared transmitter 63. In the latter case, transmitter 63 will preferably comprise a commercially available battery-powered infrared transmitter (analogous to those used to control television sets and other electrical devices) capable of transmitting an encoded version of the signals from force-sensitive device (load cell) 64 and/or strain gage 62 using methods well-known to those of skill in the art. Note that weight-sensitive fluid support means may comprise one or more of the weight-sensitive fluid supports of the type schematically illustrated in FIGS. 12A–E. When a plurality of fluid supports is used, processor means 34 is programmed to serially poll the individual fluid supports to obtain individual signals which may be combined (preferably summed) to form a signal indicative of (total) fluid source weight.

Figure 9:
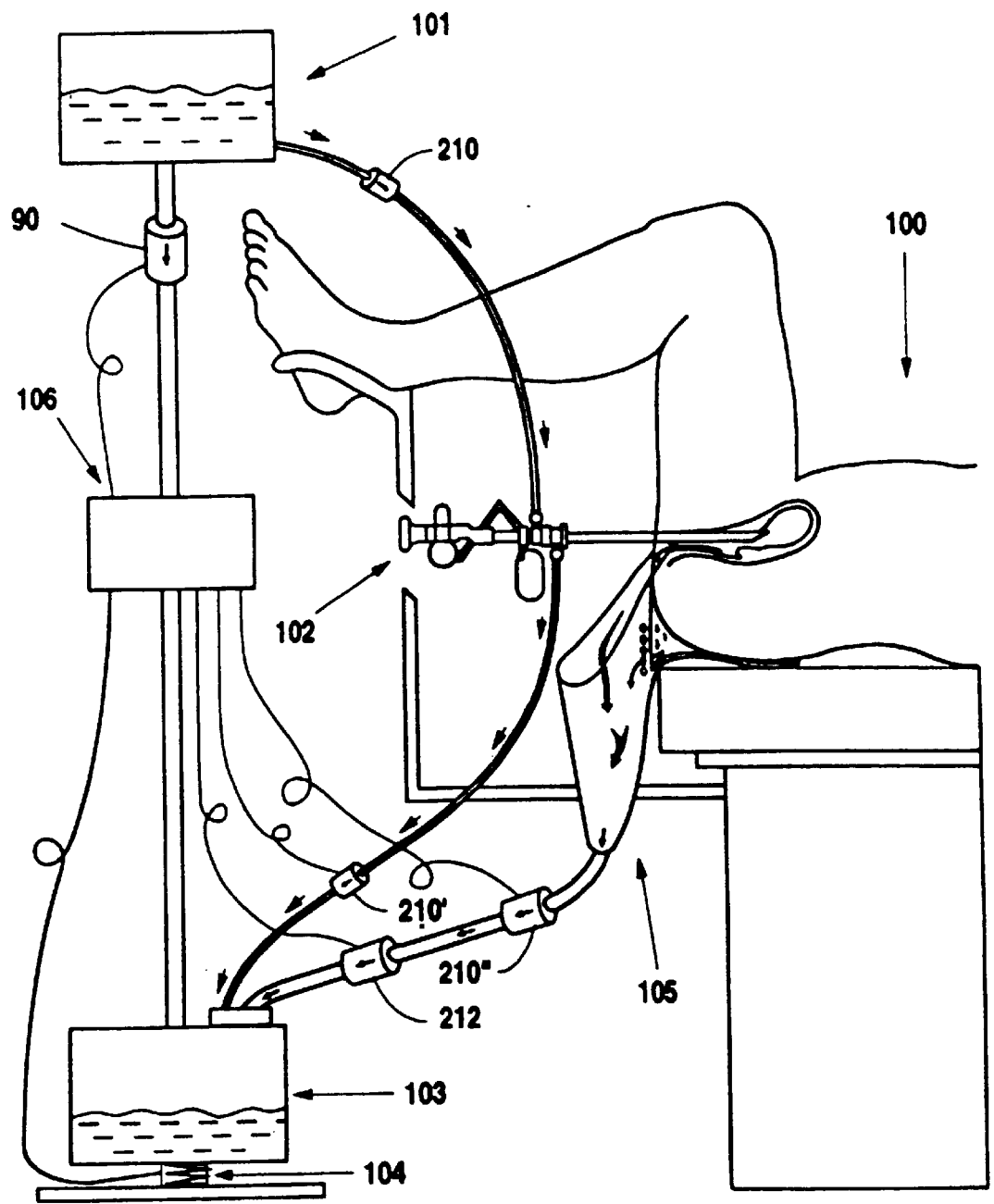
FIG. 9 schematically illustrates use of the present invention wherein irrigation fluid absorption (rate and volume) and blood loss (rate and volume) are within predetermined limits, causing no alarm.
Figure 10:
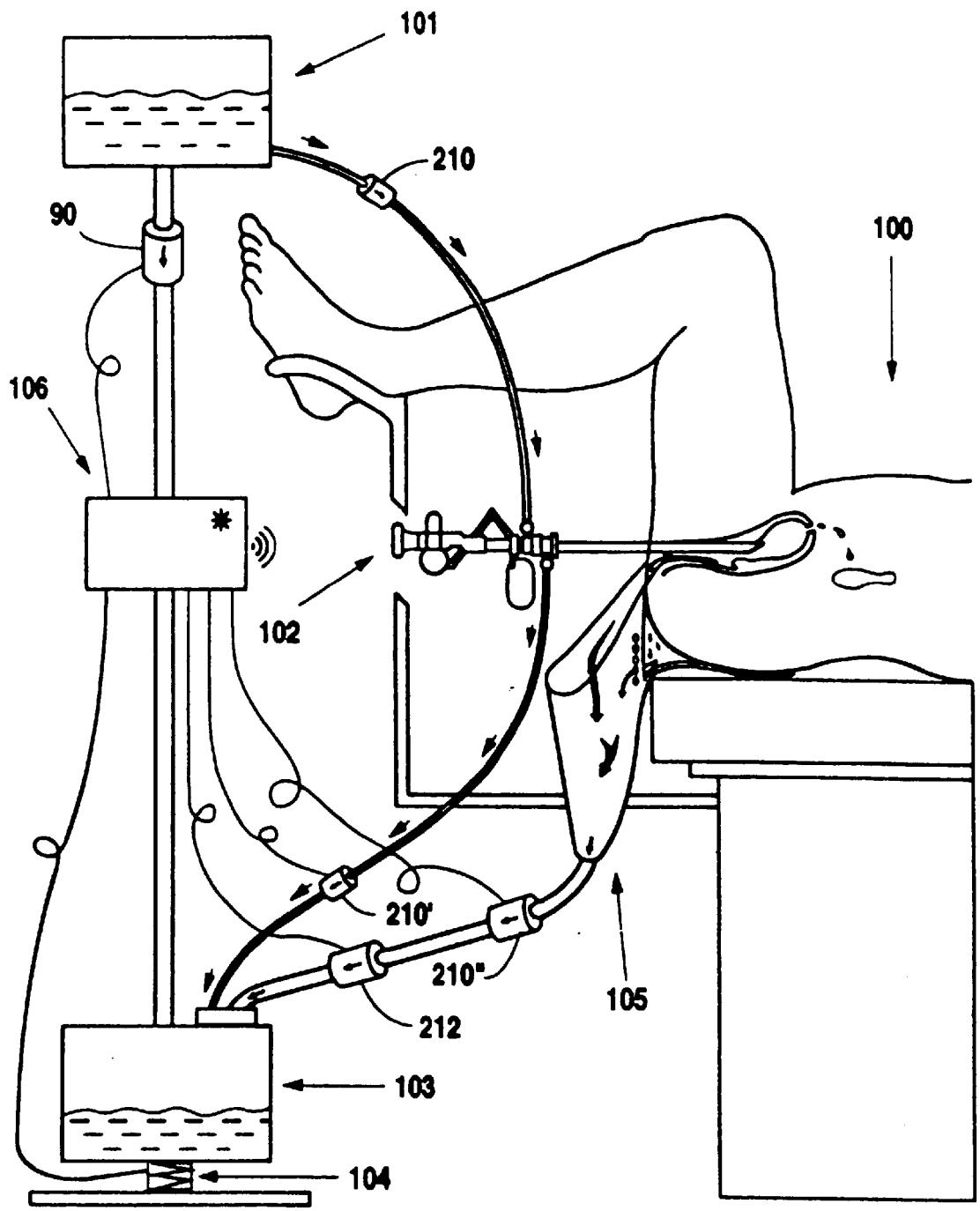
FIG. 10 schematically illustrates use of the present invention wherein irrigation fluid absorption (rate and volume) and blood loss (rate and volume) are not within predetermined limits, causing an alarm.

FIGS. 9 and 10 schematically indicate how one embodiment of the present invention would work in practice. Irrigation fluid from source 101 flows by gravity through direct-reading flow rate meter 210 to endoscope 102 which is inserted in patient 100. Waste irrigation fluid containing no blood flows by gravity from endoscope 102 through direct-reading flow rate meter 210' to waste fluid collector 103. Waste irrigation fluid (possibly including blood) also flows by gravity from patient 100 (via fluid collection drape 105) through hemoglobin analyzer 212 and direct-reading flow rate meter 210" to waste fluid collector 103. The weight of fluid source 101 bears on in-line force-sensing assembly 90, and the weight of fluid collector 103 (plus the weight of fluid source 101) bears on weight-sensitive device 104 (device 104 comprising an anti-rotation spring 91 in parallel with an LVDT, as in FIG. 2). Weight-sensitive devices 104 and 90 and (in certain embodiments) direct-reading flow rate meters 210,210',210" and hemoglobin analyzer 212 transmit signals to computing means 106 via input-output section 30. When signals from weight-sensitive devices 104 and 90 (and/or signals from direct-reading flow rate meters 210, 210',210") indicate that fluid is not being absorbed and blood is not being lost in excess of predetermined limits stored in computing means 106, no alarm is set (see FIG. 9). On the other hand, if blood loss volume is small compared to absorbed fluid volume, the weight bearing on weight-sensitive device 104 will be reduced over time, eventually falling below a predetermined limit stored in memory means 32 of computing means 106 and causing an alarm to be set (see FIG. 10). A variety of other criteria for alarm conditions, including fluid flow changes due to faults in the fluid pathways, excessive rate of blood loss, or excessive total volume of blood loss, may also be programmed into digital computer memory means 32 within computing means 106 to result in other alarm conditions.

FIG. 13 schematically illustrates a preferred embodiment of hemoglobin analyzer 212. A measured amount of waste irrigation fluid (which may contain blood) is admitted to the analyzer 212 through metering valve 221. The waste irrigation fluid is diluted (preferably 1:1) in vessel 225 with distilled water from vessel 222 through metering valve 223. Dilution with distilled water makes the diluted waste irrigation fluid hypotonic and causes osmotic lysis of any red blood cells present. Diluted waste irrigation fluid is then admitted to vessel 233 through mixing valve 227 and mixed there with Drabkin's solution (preferably 20 $\mu$l diluted waste irrigation fluid to 5 ml Drabkin's solution) admitted to the vessel through metering valve 231. Following mixture with Drabkin's solution, any hemoglobin present is converted to cyanmethemoglobin and the diluted waste irrigation fluid is admitted to a spectrophotometer 235 wherein the optical density at 540 mm is measured and converted to a signal indicative of the hemoglobin concentration which is coupled ma input-output section 30 to computing means 106. Compensation of the hemoglobin concentration signal in computing means 106 (as by multiplication by a predetermined constant stored in memory means 32) yields estimated hemoglobin concentration in the waste irrigation fluid. Multiplication of estimated hemoglobin concentration by the waste irrigation fluid flow rate indicated by direct-reading flow rate meter 210" yields a lost hemoglobin flow rate. Division of the lost hemoglobin flow rate by the patient's actual hemoglobin concentration in circulating blood yields an estimated blood loss flow rate from the patient which can be compared to a predetermined limit stored in memory means 32 of computing means 106 preparatory to setting of an alarm. Note that waste irrigation fluid from endoscope 102 would preferably be similarly tested if it contained significant blood. If such testing yields a clinically significant blood loss flow rate from the endoscope drain, the blood loss flow rates from the patient and the endoscope would be added to provide a total blood loss flow rate, which would then be compared with a stored predetermined limit as above preparatory to setting of an alarm. Note also that fluid flow through the above hemoglobin analyzer would normally result in elimination of any gas bubbles in the fluid prior to its admission to the spectrophotometer 235.

An optical comparator 312 of the present invention, which may replace or supplement hemoglobin analyzer 212 as described above, is schematically illustrated in FIGS. 14, 14A, 15 and 15A. A light source 310 produces light at one or more discrete wavelengths. At least a portion of the light from source 310 passes through transmission optical components of adjustable diffuser means 320 which is coupled to light source 310 by (preferably) opaque housing 311. Note that adjustable diffuser means 320 may also comprise reflective optical components either substantially alone or in combination with transmission optical components. At least a portion of the variably scattered light emanating from adjustable diffuser means 320 then is intercepted by comparator chambers 332,333 which are coupled to diffuser means 320 by (preferably) opaque housing 321 and which are filled receptively with optical reference fluid and sample fluid. The walls of comparator chambers 332,333 are formed by the preferably substantially opaque) chamber housing 330, optical windows 340,340' and (preferably substantially opaque) chamber divider 335. Fluid may be introduced into the chambers through inlet ports 300,301, and it may be removed through outlet ports 300',301' respectively.

Output light emanates from comparator chambers 332, 333 which intercept the variably scattered light from the adjustable diffuser means. At least a portion of the output light emanating from each chamber impinges on a detector 350 which is coupled to chamber housing 330 by (preferably) opaque housing 331 and which in the illustrated embodiment comprises two light receptors 352,353. Receptor 352 produces a signal substantially proportional to a parameter of light emanating from chamber 332 and impinging on corresponding receptor 352, while receptor 353 produces a signal substantially proportional to a parameter of light emanating from chamber 333 and impinging on corresponding receptor 353. Note that light receptors 352, 353 are preferably separated by a substantially opaque divider 336 to preserve correspondence of receptor 352 with chamber 332 and correspondence of receptor 353 with chamber 333. Signals from receptors 352,353 are transmitted to comparing means 355 over (wired or wireless) channel 351 to produce a comparator signal which may be displayed and/or used in subsequent calculations related, for example, to estimation of hemoglobin concentration and/or fat concentration in fluid within a comparator chamber. Note that comparing means 355 may compare light amplitude, frequency and phase shift, for example, to produce a comparator signal having one or more components which effectively distinguishes various physical and/or chemical properties of sample and reference fluids and/or components (substantially fluid and/or substantially solid) thereof.

What is claimed is:

1. An optical comparator, comprising a light source;

adjustable diffuser means proximate said light source and intercepting at least a portion of light from said light source to produce variably scattered light emanating from said adjustable diffuser means;

at least two comparator fluid chambers positioned to intercept at least a portion of said variably scattered light to produce output light emanating from each of said comparator fluid chambers;

a detector comprising a plurality of light receptors, at least a portion of output light emanating from each of said comparator fluid chambers impinging on a light receptor corresponding to each of said comparator fluid chambers, and each said corresponding light receptor producing a signal substantially proportional to a parameter of said intercepted portion of output light impinging on said receptor; and comparing means for comparing each said light receptor signal to at least one other said light receptor signal to produce a comparator signal.

* * * * *